United States Patent [19]

Terano et al.

[11] Patent Number: 5,656,434
[45] Date of Patent: Aug. 12, 1997

US005656434A

[54] MONOCLONAL ANTIBODY AGAINST CARDIAC GLYCOSIDE AND UTILIZATION THEREOF

[75] Inventors: Yoshitake Terano, Ikeda; Hiroshi Nakazato, Ibaraki, both of Japan

[73] Assignee: Suntory Limited, Osaka, Japan

[21] Appl. No.: 280,553

[22] Filed: Jul. 26, 1994

Related U.S. Application Data

[63] Continuation of Ser. No. 923,898, filed as PCT/JP91/01267, Sep. 24, 1991, published as WO92/12252, Jul. 23, 1992, abandoned.

[30] Foreign Application Priority Data

Dec. 28, 1990  [JP]  Japan ................... 2-418581

[51] Int. Cl.⁶ .................................. G01N 33/53
[52] U.S. Cl. .................... 435/7.1; 436/501; 436/547; 436/548; 436/817; 436/161; 530/388.24; 530/388.9; 530/389.2; 530/389.8
[58] Field of Search .................... 530/388.1, 388.24, 530/388.5, 388.4, 389.2, 384.8; 435/7.9, 7.1; 436/547, 548, 815, 817, 501, 161

[56] References Cited

U.S. PATENT DOCUMENTS

| | | | |
|---|---|---|---|
| 4,606,855 | 8/1986 | Deutsch et al. | 530/387 |
| 5,164,296 | 11/1992 | Blaustein et al. | 435/7.24 |

FOREIGN PATENT DOCUMENTS 60-110289  6/1985  Japan.

OTHER PUBLICATIONS

H.-U. Simon et al., "Production and Characterization of a High Affinity Monoclonal Anti–Digoxin and Anti–Digitoxin Antibody", *Allergie und Immunologie*, vol. 36, No. 4, pp. 343–350 (1990).

I.R. Kehayov et al., "Generation of Monoclonal Anti–Digoxin Antibodies", *Hybridoma*, vol. 9, No. 5, pp. 493–510 (1990).

D. Buchman et al., "Monoclonal Antibodies to Digoxin: Comparison of In Vitro and In Vivo Immunization", *Hybridoma* vol. 4, No. 2, pp. 173–177 (1985).

Collignon et al., Hybridoma, vol. 7, No. 4, pp. 355–366 (1988) "Specific Binding Chracteristics of High Affinity Monoclonal Antidigitoxin Antibodies".

Terano et al "Production & Characterization of Antibodies to Ouabain" Jpn. J. Med. Sci. Biol. 44 123–139 (1991).

Masugi et al "Circulating Factor with Ouabain–Like Immunoreactivity In Patients with Primary Aldosteronism" Biochem. Biophys. Res. Comm. 135 (1986) 41–45.

Hunter et al "High–Affinity Monoclonal Antibodies to the Cardiac Glycoside, Digoxin" J. of Imm. 129 (1982) pp. 1165–1172.

Ahmed et al "Intraction of (Na⁺, K⁺)–ATPases & Digitalis Genins" J. Biol. Chem. 258 (1983) pp. 8092–8097.

*Primary Examiner*—Lora M. Green
*Attorney, Agent, or Firm*—Burns, Doane, Swecker & Mathis, L.L.P.

[57] ABSTRACT

The present invention provides monoclonal antibodies that specifically recognize a specific structural portion of cardiac glycoside.

The monoclonal antibodies of the present invention recognize an integrated structure in the steroid structure of cardiac glycoside or its aglycon comprising: a D-ring bonded in the cis-configuration with respect a C-ring; a methyl group bonded in the β-configuration at the C13 position; a hydroxyl group bonded in the β-configuration at the C14 position; and, an α, β-unsaturated lactone group bonded in the β-configuration at the C17 position. This structure is common to cardiac glycoside substances that inhibit potassium ion concentration antagonist type Na⁺,K⁺-ATPase.

3 Claims, 15 Drawing Sheets

Preparation of Immunogen

Results of Antigen Capturing (ELISA) of the Monoclonal Antibody of the Present Invention

Cross Reactivity of the Monoclonal Antibody of the Present Invention and Various Cardiac Glycosides and their Aglycons Ouabain —○—
Digoxin —●—
Ouabagenin —□—
Digoxigenin —■—
Rhamnose —△—
Hydrocortisone —◆—
Digitoxose —▲—

Relationship Between Radioactivity and Cardiac Glycoside
Concentration in Scintillation Proximity Assay Using
the Monoclonal Antibody of the Present Invention —○— Monoclonal Antibody 249F8
—●— Monoclonal Antibody 278A9
—△— Antigen-Unsensitized Mouse Antibody Fraction

Relationship Between Absorbance and Cardiac Glycoside Concentration in ELISA Using the Monoclonal Antibody of the Present Invention Ouabain ──○──
Digoxin ──●──

Structural Portion Recognized by the Monoclonal Antibody of the Present Invention (wherein, R represents:)

Relationship Between Absorbance and the Concentration of Human Plasma Ouabain-Like Factor (OLF) Fraction in ELISA Using the Monoclonal Antibody of the Present Invention Relationship Between Absorbance and Digoxin Concentration when Measured by Antibody Capturing (ELISA) and the Measuring Method of the Japanese Pharmacopeia (Keller-Kiliani Method)

Affinity Between Cardiac Glycosides and the Antibody of the Present Invention

MONOCLONAL ANTIBODY AGAINST CARDIAC GLYCOSIDE AND UTILIZATION THEREOF

This application is a continuation of application Ser. No. 07/923,898, filed as PCT/JP91/01267, Sep. 24, 1991, published as WO92/2252, Jul. 23, 1992, now abandoned.

TECHNICAL FIELD

The present invention relates to monoclonal antibodies that recognize the structural portion that contains the D-ring bonded in a cis-configuration of the steroid structural portion of a cardiac glycoside, along with their utilization.

BACKGROUND ART

Polyclonal antibodies are known that react specifically with digoxin, but do not cross-react with steroid hormones (Smith, T. W. et al., Biochemistry 9(2), 331–337, 1970). In addition, monoclonal antibodies are known that have strong affinity for digoxin (Hunter, M. M. et al., J. Immunol. 129(3), 1165–1172, 1982). Moreover, it is also recognized that monoclonal antibodies to digoxin demonstrate a strong neutralizing action against digoxin effects in guinea pig atrium (Wong, P. C. et al., Eur. J. Pharmacol. 136, 437–440, 1987). However, there are no detailed findings concerning the site that is recognized by these monoclonal antibodies in terms of the structure of digoxin.

Note, the inventors of the present invention have produced polyclonal antibodies to ouabain and reported that they react with cardiac glycoside, especially ouabain, digoxin, and endogenous ouabain-like substances (Masugi, F. et al., Biochem. Biophys. Res. Commun. 135(1), 41–45, 1986).

Although antibodies having clearly defined specificities are required for the accurate measurement of blood concentrations of cardiac glycosides in various forms of research and clinical applications of cardiac glycosides, as was previously stated, such antibodies are presently not known. Thus, the present invention provides monoclonal antibodies that specifically react only with cardiac glycoside having a specific structure.

DISCLOSURE OF THE INVENTION

As a result of various studies conducted by the inventors to solve the above-mentioned problems, the inventors succeeded in producing hybridomas that produce monoclonal antibodies which specifically recognize the structural portion containing the D-ring bonded in a cis-configuration within the steroid structure of cardiac glycoside by using an immunogen wherein bovine serum albumin is covalently bonded to the sugar portion of ouabain, thereby completing the present invention. Moreover, the inventors discovered that the monoclonal antibodies of the present invention specifically react with substances that inhibit the potassium ion concentration antagonist type $Na^+,K^+$-ATPase.

Thus, the inventors provide monoclonal antibodies that recognize an integrated structure comprising: the D-ring bonded in the cis-configuration; a methyl group bonded in the β-configuration at the C13 position; a hydroxyl group bonded in the β-configuration at the C14 position; and an α,β-unsaturated lactone group bonded in the β-configuration at the C17 position in the steroid structure of cardiac glycoside or its aglycon.

Moreover, the present invention also provides monoclonal antibodies that recognize the structure of the common portion of steroid substances that inhibit $Na^+,K^+$-ATPase activity in the same formas ouabain, or in other words, in the form of a potassium ion concentration antagonist.

The present invention also provides hybridomas that produce the above-mentioned monoclonal antibodies.

Moreover, the present invention also provides the use of the above-mentioned monoclonal antibodies.

DETAILED DESCRIPTION

Figure 1:
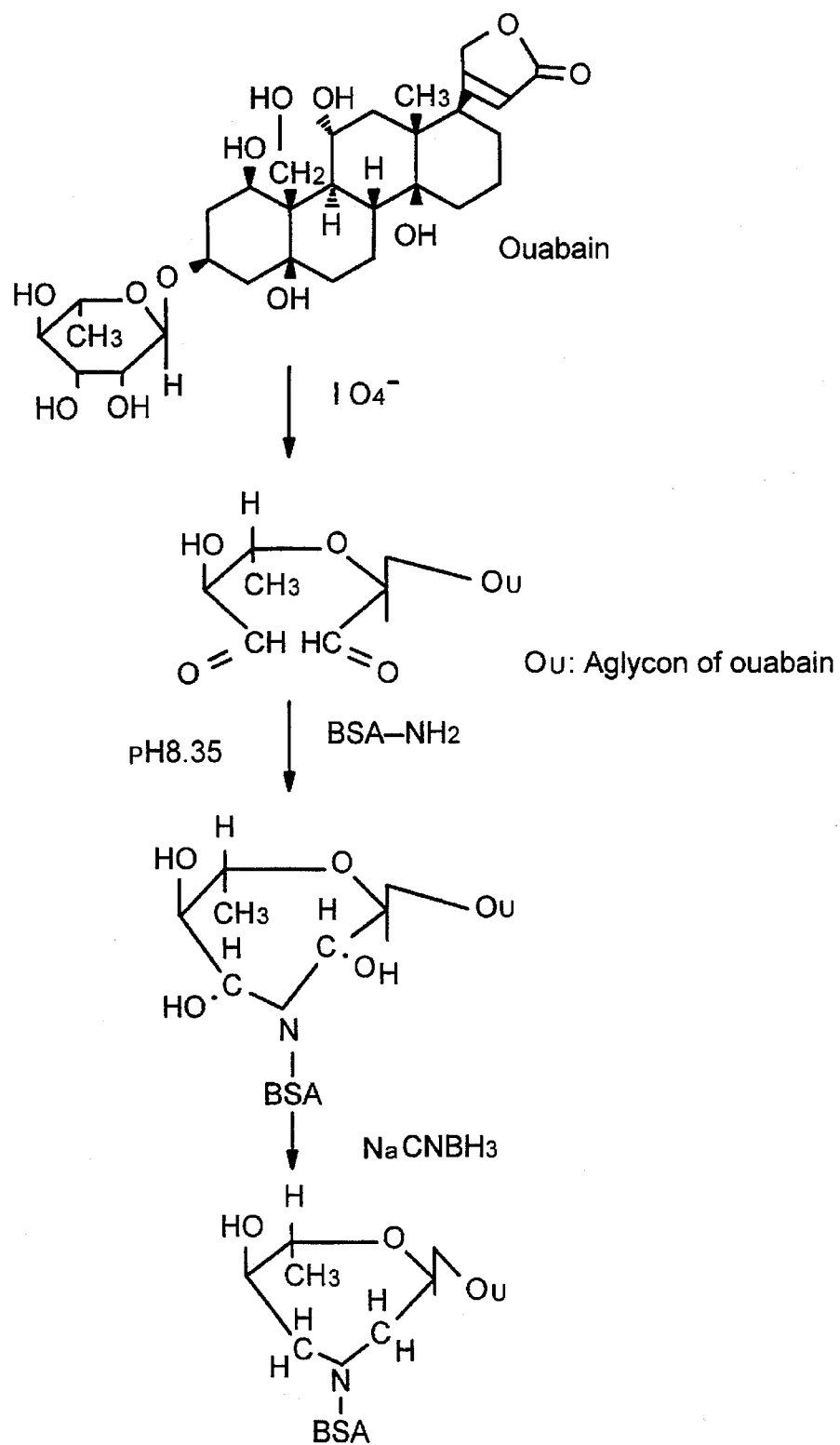
FIG. 1 is a reaction scheme indicating the preparation method of the immunogen for producing the hybridomas of the present invention.

Although various cardiac glycosides can be used for an immunogen for producing hybridomas that produces monoclonal antibodies of the present invention, a specific example of a cardiac glycoside that can be used is that wherein bovine serum albumin is covalently bonded to the sugar portion of ouabain. For example, after cleaving the sugar portion of ouabain with periodic acid ion, the resulting two aldehyde groups are reacted with the free amino group of the bovine serum albumin. The immunogen can then be prepared by removal of the resulting hydroxyl group by reduction. One example of this is described in Example 1, and the reaction scheme is indicated in FIG. 1.

Figure 2A:
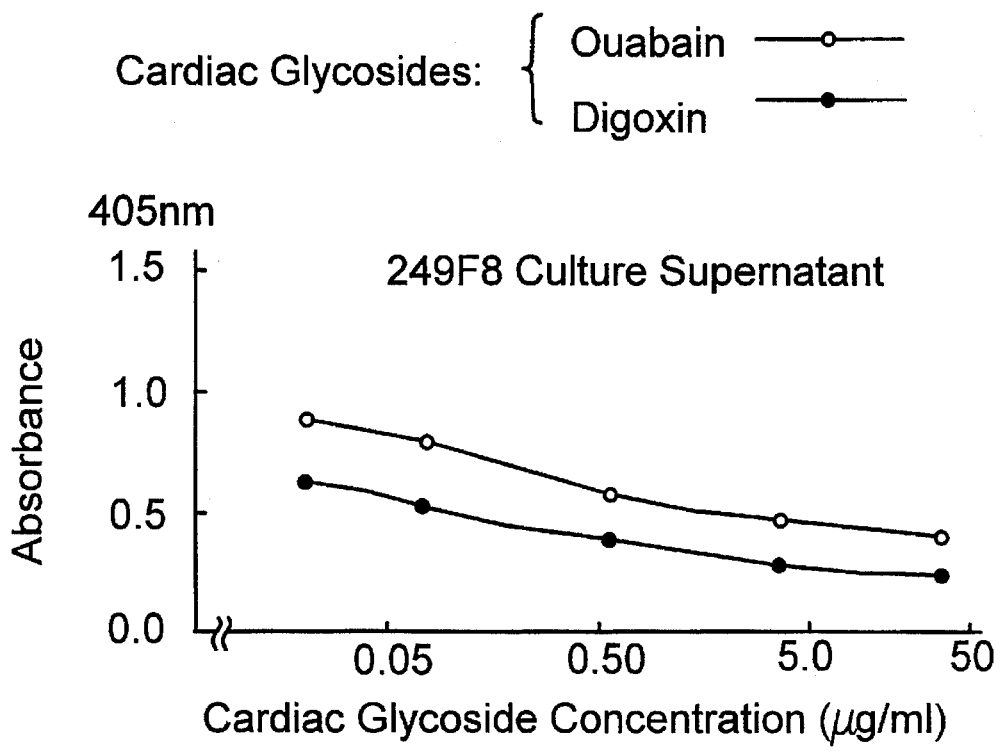
FIGS. 2(A) and 2(B) gives graphs indicating the reactivity of the monoclonal antibodies 249F8 (FIG. 2A) and 278A9 (FIG. 2B) in the culture supernatant of the hybridomas of the present invention with ouabain and digoxin in the ELISA antibody capture method.
Figure 2B:
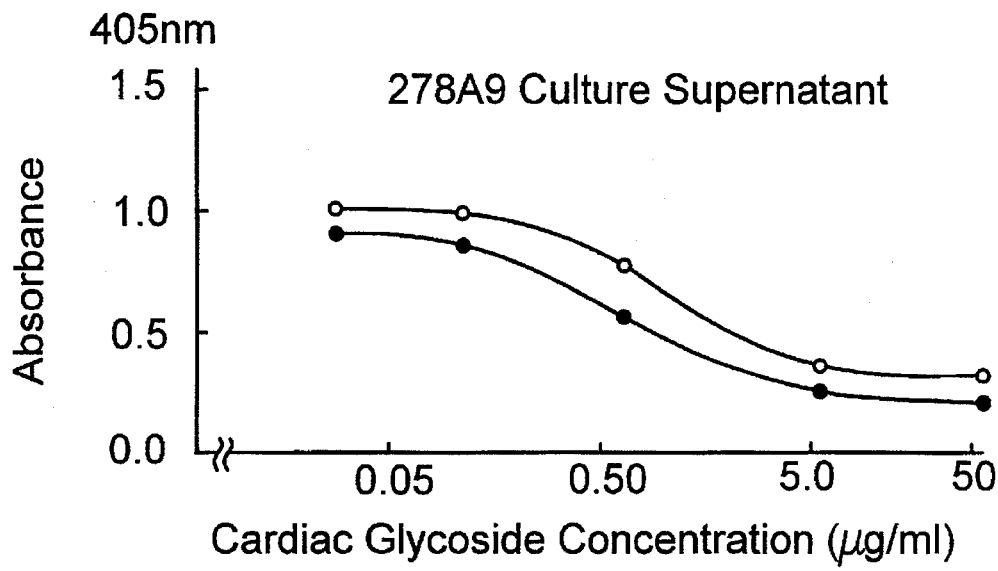

Production of the hybridomas can be performed according to commonly used methods (Koehler, G. et. al., Nature 256, 495–497, 1975). One example of this is described in Example 2. As a result, 10 strains of hybridomas were obtained that produce monoclonal antibodies that react with ouabain. By further screening these hybridomas by the ELISA antibody capture, method hybridomas 249F8 and 278A9 were obtained that produce monoclonal antibodies which quantitatively react with both ouabain and digoxin. The results of ELISA antibody capture method on the culture supernatants of these hybridomas are indicated in FIG. 2.

The monoclonal antibody of the present invention can be produced by in vitro or in vivo culturing of, for example, the above-mentioned hybridomas. A specific example of in vivo culturing is described in Example 3. In the in vitro method, after culturing the hybridomas of the present invention using commonly used methods, monoclonal antibodies can be isolated and purified according to the same purification method described in Example 3 for in vivo cultures. When the titer of the monoclonal antibody of the present invention produced in this manner was measured by ELISA, the titer was 4,300 units/mg for monoclonal antibody 249F8 (the monoclonal antibody produced from hybridoma 249F8), and the titer was 2,200 units/mg for monoclonal antibody 278A9 (the monoclonal antibody produced from hybridoma 278A9).

A study of the cross-reactivity of the monoclonal antibodies of the present invention with respect to various substances was conducted for the 46 substances indicated in Table 1 of Example 4. Those results are indicated in Table 3 and FIG. 3. Based on these results, those substances were divided into those which react with monoclonal antibodies of the present invention (referred to as Type I substances), and those which do not react (referred to as Type II substances). It was discovered that all of the Type I substances that react with the monoclonal antibodies of the present invention are either cardiac glycosides or their aglycons, and that all such substances possess a commonly shared structure indicated by the solid lines in formula (I) below, or in other words, an integrated structure comprising: a D-ring bonded in the cis-configuration with respect to C-ring; a methyl group bonded in the β-configuration at the C13 position; a hydroxyl group bonded in the β-configuration at the C14 position; and an α,β-unsaturated lactone group bonded in the β-configuration at the C17 position.

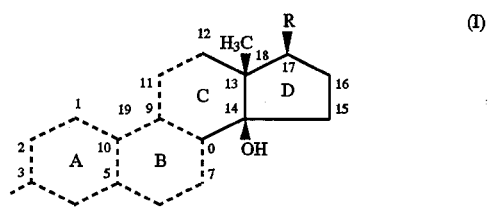

wherein, R represents the following cardenolide or bufagenolide form:

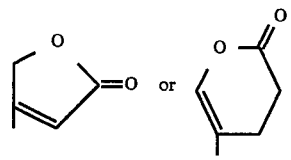

Furthermore, the sites indicated with dotted lines in the above-mentioned structure indicate those sites within the steroid structure which have essentially no effect on recognition by the monoclonal antibodies of the present invention. The above-mentioned properties are common for both monoclonal antibodies 249F8 and 278A9 of the present invention. Moreover, that which recognizes the above-mentioned structured such as the compound expressed in, for example, formula (II):

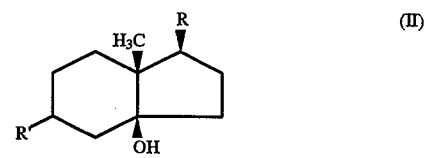

wherein, R has the same meaning as described above, and R' indicates a piperizyl group, a piperizino group, or its derivative, is also included in the present invention even if it is an antibody that cross reacts with other substances.

Next, the potassium ion concentration antagonist type (ouabain type) $Na^+,K^+$-ATPase inhibitory activity was examined for several of the substances indicated in Table 1. Those results are indicated in Table 2. These results clearly indicate that all substances that demonstrate cross-reactivity with a monoclonal antibody of the present invention possess activity which inhibits the above-mentioned enzyme.

The results relating to cross-reactivity, as well as the results of the potassium ion concentration antagonist type $Na^+,K^+$-ATPase inhibitory activity (Table 2), are indicated in Table 3 along with the presence or absence of the specific structure shown in the above-mentioned formula (I). As is clear from this table, the specific structural portion recognized by the monoclonal antibody of the present invention is also present in those substances demonstrating activity that inhibits the potassium ion concentration antagonist type $Na^+,K^+$-ATPase. Thus, the specificity of the monoclonal antibodies of the present invention can be used for screening, isolation, purification, and measurement, etc. of physiologically active substances possessing activity that inhibits potassium ion concentration antagonist type $Na^+,K^+$-ATPase.

Known methods can be used for measurement, detection, or selection of physiologically active substances possessing inhibitory action against potassium ion concentration antagonist type $Na^+,K^+$-ATPase, using the monoclonal antibodies of the present invention. For example, this may be performed in the manner of the examples subsequently described.

In other words, the monoclonal antibody of the present invention is first adsorbed and fixed onto the surface of a suitable solid carrier. Next, this antibody is brought in contact with the sample. As a result, the test substance within the sample specifically bonds with the monoclonal antibody fixed on the solid carrier. Consequently, the test substance within the sample is fixed to the solid carrier by means of the monoclonal antibody fixed onto the solid carrier in advance.

Next, the above-mentioned carrier serving as a secondary carrier, is brought in contact with, for example, a solution containing a polyclonal antibody to the test substance and an anti-mouse IgG antibody. Consequently, said polyclonal antibody bonds with any secondary epitopes of the test substance that were not used in bonding with the monoclonal antibody. As a result, said secondary antibody bonds with the solid carrier by means of the monoclonal antibody and test substance that had been fixed in advance. In this case, the amount of secondary antibody that is fixed reflects the amount of test substance in the sample, or in other words, the amount of fixed test sample.

Thus, by measuring the amount of fixed secondary antibody, the amount of test substance in the sample can be determined. A detailed description of the method for measuring the amount of fixed secondary antibody is subsequently provided.

In the above-mentioned method, for example, microtiter plates, such as microtiter plates made of polyvinyl chloride or microtiter plates made of polystyrene, can be used for the solid carrier. Fixation of the monoclonal antibody can be performed, for example, by diluting the monoclonal antibody in a suitable buffer, such as a carbonate buffer or phosphate buffer, applying this buffer solution to the surface of the solid carrier, and then incubating for at least 30 minutes at a temperature of 4°–37° C.

Next, the unabsorbed monoclonal antibody is removed by washing the solid carrier several times with a washing solution, such as a buffer containing a surfactant like Tween 20. Examples of this washing solution include phosphate buffer, Tris buffer, and borate buffer.

Next, in order to block free bonding groups present on the surface of the solid carrier, the solid carrier is treated with a blocking buffer. This blocking buffer is, for example, a buffer containing 1 to several percent bovine serum albumin (BSA), egg white albumin, skim milk or the like. Examples of buffers that can be used include phosphate buffer, Tris buffer, borate buffer and the like. Treatment can be performed by incubating for at least 30 minutes at a temperature of 4°–37° C.

Next, the blocking buffer is removed by washing the solid carrier. This washing can be performed in the same manner as in the above-mentioned washing, following fixation of the monoclonal antibody. Thus, preparation of the solid carrier is completed.

Next, this solid carrier is brought in contact with a sample diluted in a suitable buffer such as a phosphate buffer, Tris buffer, or borate buffer. This contact can be performed by incubating for at least 30 minutes at a temperature of 4°–37° C. The solid carrier is then washed in the manner described above.

Next, a buffer containing the secondary antibody is brought in contact with the above-mentioned solid carrier. Examples of buffers that can be used in this case include a phosphate buffer, Tris buffer, and borate buffer. This contact can be performed by incubating for at least 30 minutes at a temperature of 4°–37° C. The solid carrier is then washed in the manner described above.

Next, detection and measurement of the secondary antibody fixed in the manner described above can be performed according to any conventional method. It is also possible to label the secondary antibody itself, such as by using radionuclides, fluorescent substances, or enzymes, and perform detection and measurement directly. However, the preferred method of the present invention involves using a specific tertiary antibody labeled by various methods to the secondary antibody.

The tertiary antibody is an antibody of an animal species different from the species of animal used in preparation of the secondary antibody. There is used an antibody or its fragment to the immunoglobulin of the animal species used in preparation of the secondary antibody. For example, in the case the secondary antibody was prepared using a rabbit, a goat antibody to rabbit immunoglobulin can be used for the tertiary antibody.

Conventional labelling substances can be used to label the tertiary antibody. Examples of these substances include radionuclides such as $^{125}$I, $^{3}$H and $^{14}$C; fluorescent substances such as fluorescein isothiocyanate (FITC), rhodamine, and Texas red; and enzymes such as horseradish peroxidase, alkaline phosphatase, and urease. In the preferable mode of the present invention, an enzyme is used for labelling the tertiary antibody, and enzyme immunoassay (ELISA) is used for the sandwiching method of the present invention. A substrate corresponding to the enzyme, and preferably a color forming enzyme substrate, is used for detection of the enzyme. For example, in the case of using peroxidase for the enzyme, hydrogen peroxide is used for the substrate, while examples of coloring reagents that can be used include ortho-phenylene diamine and 3,3',5,5'-tetramethylbenzidine.

In addition, in the above-mentioned method, the primary and secondary antibodies may be used interchangeably. Moreover, in the present invention, in addition to the above-mentioned measuring method, enzyme linked immunosorbent assay or radioimmunoassay may be performed according to conventional methods using a labelled antigen together with the monoclonal antibody.

The present invention also provides a measuring kit. This kit at least contains a monoclonal antibody of the present invention. The monoclonal antibody may be in solution or freeze-dried, or may also be fixed to a solid carrier. In the case the kit contains a monoclonal antibody fixed to a solid carrier, this solid carrier is preferably contained in the kit after having been treated with a blocking agent.

The measuring kit can also include a secondary and tertiary antibody as its third element. In the case the label of the secondary and tertiary antibody in this case is an enzyme, the kit can also include a coloring reagent which contains the substrate of the enzyme. However, commercially available products can be used for the labelled secondary and tertiary antibody as well as the corresponding coloring reagent are not essential elements of the kit of the present invention.

The measuring kit of the present invention can also contain a sample dilution buffer, various types of reagent dilution buffers, a washing solution, standard antigens, etc. as optional elements.

Moreover, the method for collecting a physiologically active substance that possesses potassium ion concentration antagonist type Na$^+$,K$^+$-ATPase inhibitory activity using the monoclonal antibody of the present invention can also be antigen collection methods using ordinary antigen-antibody reactions.

Figure 4A:
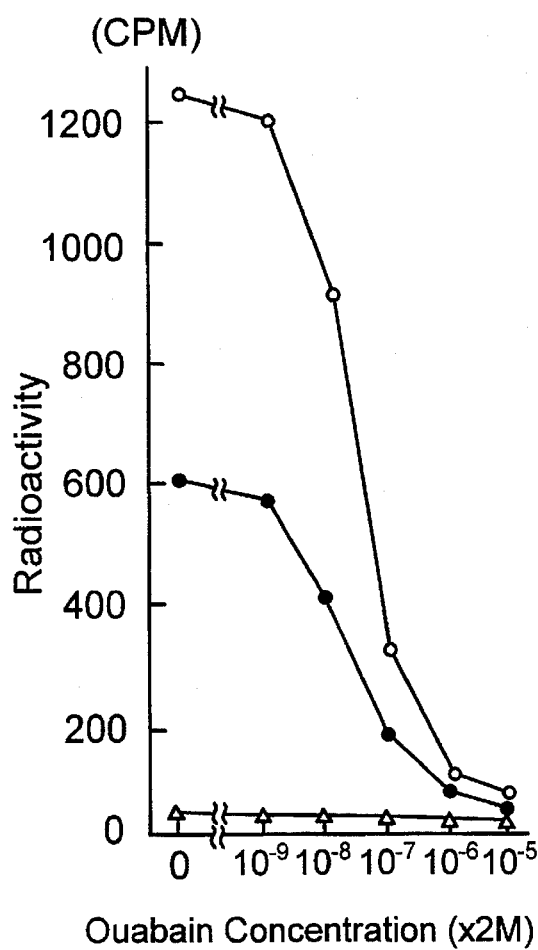
FIGS. 4(A) and 4(B) gives graphs indicating the relationship between measured radioactivity values and the concentrations of ouabain (FIG. 4A) and digoxin (FIG. 4B) as measured by scintillation proximity assay using monoclonal antibodies of the present invention.
Figure 4B:
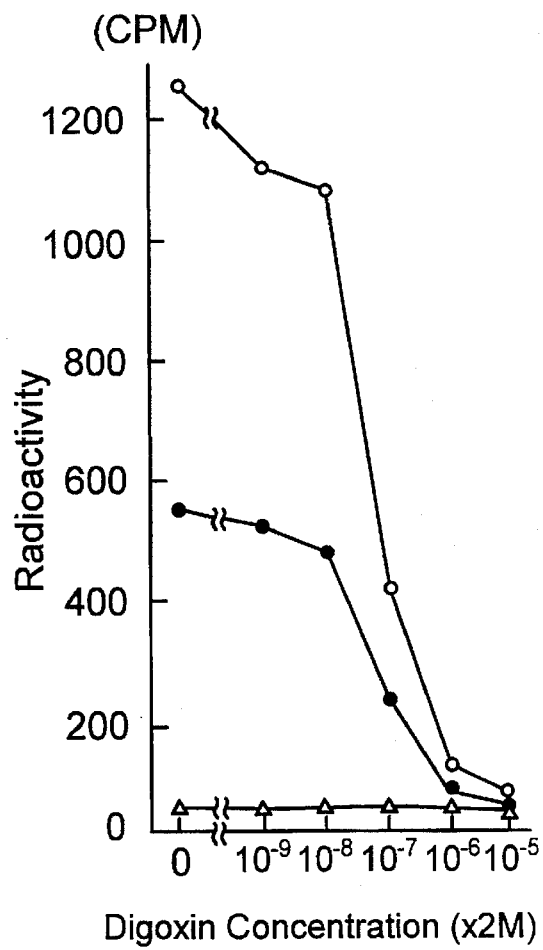

An example of measurement of cardiac glycoside (potassium ion concentration antagonist type Na$^+$,K$^+$-ATPase inhibitory substance) using a monoclonal antibody of the present invention is indicated in Example 5. In this example, ouabain and digoxin are used as cardiac glycosides, and the relationship between their concentrations and radioactivity measured values (CPM) in scintillation proximity assay (SPA) is indicated in FIG. 4.

Figure 5A:
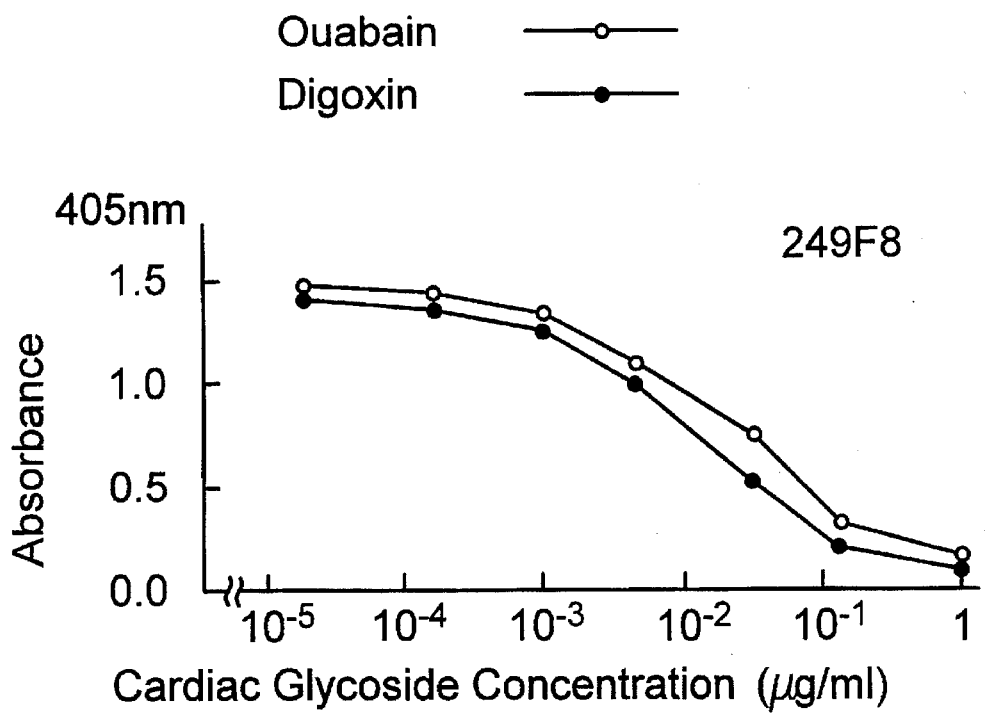
FIGS. 5(A) and 5(B) gives graphs indicating the relationship between absorbance and the concentrations of ouabain and digoxin, as measured by ELISA, using monoclonal antibodies 249F8 (FIG. 5A) and 278A9 (FIG. 5B) of the present invention.
Figure 5B:
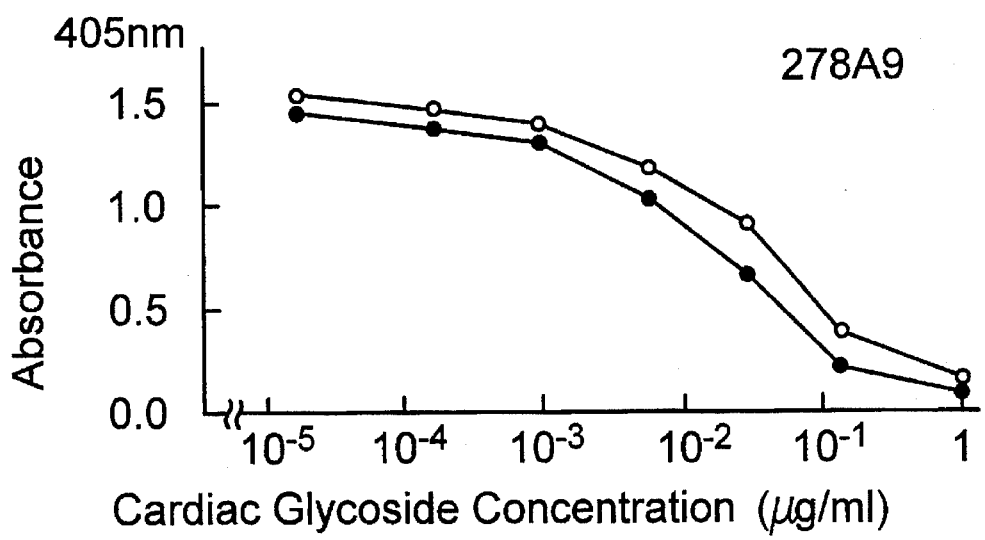
Figure 6A:
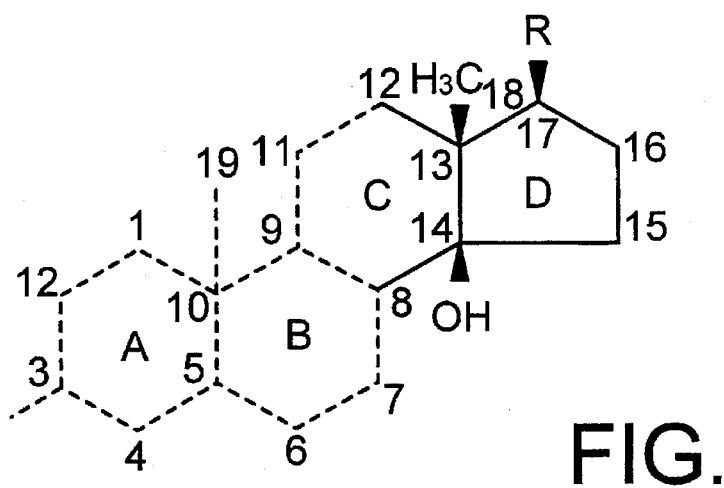
FIGS. 6(A) and 6(B) indicate the steroid structural portion of cardiac glycoside and its aglycon that is recognized by monoclonal antibodies of the present invention.
Figure 6B:
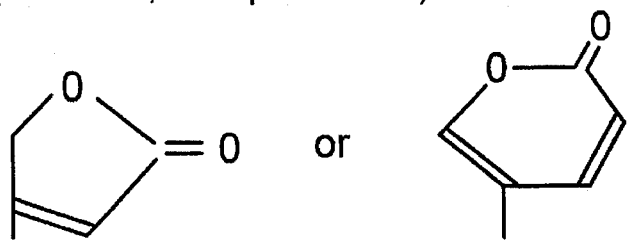

In addition, the relationship between absorbance and the concentrations of ouabain and digoxin as measured by ELISA using a method similar to that in Example 1 is indicated in FIG. 5. Each of these cases indicate that the monoclonal antibody of the present invention can be used for measurement of cardiac glycoside.

EFFECT OF INVENTION

As described above, use of the monoclonal antibodies of the present invention allows recognition of the immunochemical distribution and localization in tissue, and the isolation and quantitative analysis of cardiac active substances contained in natural substances. It also allows easy identification of properties of cardiac active substances, or in other words, potassium ion concentration antagonist type $Na^+,K^+$-ATPase inhibitory activity, for existing or new synthetic compounds. Moreover, it is expected to directly contribute to pathophysiological research pertaining to essential hypertension and various types of heart diseases, their diagnosis and treatment, as well as the creation of new drugs in these fields based on the adopting of a structural approach (receptor ($Na^+,K^+$-ATPase) antagonists of said $Na^+,K^+$-ATPase inhibitory substances resulting from the adopting of a structural approach to potassium ion concentration antagonist type $Na^+,K^+$-ATPase inhibitory activity, or in other words, the creation of therapeutic drugs for treatment of essential hypertension).

BEST MODE FOR CARRYING OUT THE INVENTION

Although the following provides a detailed explanation of the present invention through examples, the examples do not limit the scope of the present invention.

Example 1: Preparation of Immunogen

Ouabain (0.2 mM) and sodium periodate (0.25 mM) were dissolved in 5 ml of distilled water and allowed to stand for 24 hours at room temperature, then 10 ml of ethanol were added and the pH was adjusted to 8.35 with sodium hydroxide. Bovine serum albumin (2 µM) was added and the pH was adjusted to 9.35 with sodium hydroxide followed by allowing the solution to stand overnight at 4° C. Next, 0.8 mM sodium cyanoboron hydride was added, then the solution was dialyzed for 48 hours with deionized water after it was additionally dialyzed three times with distilled water followed by freeze-drying.

Thus, an ouabain-protein complex was prepared in which bovine serum albumin is covalently bonded to the terminal of the sugar chain of ouabain. According to the results of measurement of the absorbance at 370 nm in a 50% sulfuric acid solution, 33 molecules of ouabain were bonded per molecule of bovine serum albumin.

Example 2: Preparation of Hybridomas

The freeze-dried immunogen prepared in Example 1 was dissolved in a suitable amount of distilled water, then the solution was diluted with Dalvecco's PBS(−) (abbreviated as D'PBS(−)) to prepare the undiluted immunogen solution having a concentration of 0.1 mg/ml. The above-mentioned undiluted immunogen solution was mixed with Freund's complete adjuvant at a ratio of 3:2 to prepare a water-in-oil type emulsion. Initial immunization was performed by subcutaneously injecting this emulsion into BALB/C mice (SPF, females, 5 weeks old) at a dose of 20 µg of antigen per animal. Another water-in-oil type emulsion was prepared by mixing Freund's incomplete adjuvant and the above-mentioned undiluted immunogen solution at a ratio of 3:2 which was then used for additional immunization by intraperitoneal injection into mice at a dose of 10 µg of antigen per animal. Additional immunization was performed three times at 3-week intervals (4 times including the initial immunization). 1 week to 10 days after the final immunization, test samples were taken from the fundus venous nidus. The titer of serum antibody was then measured by ELISA, to be subsequently described, and those mice that were sensitized were selected. 20 µg of antigen per animal was intravenously injected into the mice 3 days before performing cell fusion.

Note, the above-mentioned ELISA procedure was performed as described below. Firstly, aqueous solutions (1 mg/ml) of each of the antigens (ouabain-BSA complex, ouabain, digoxin, and bovine serum albumin) were prepared. These were diluted to a concentration of 10 µg/ml with coating buffer (0.1 M carbonate buffer, pH 9.6). These solutions were then distributed into each well of a microtiter plate placing 100 µl in each well. The plates were then allowed to stand overnight at 4° C. The supernatant was suctioned from the plate and the plate was washed three times with washing solution (D'PBS(−) containing 0.1 w/v % Tween 20 and 0.1 w/v % $NaN_3$). Next, 150 µl of blocking solution (D'PBS(−) containing 0.1% (w/v) $NaN_3$ and 0.1% (w/v) gelatin) were added to each well followed by incubation for 30 minutes at 37° C. After removing the blocking solution, the plate was washed three times with washing solution. Next, 100 µl of sample (primary antibody) (serum diluted solution) were added to each well followed by incubation for 1 hour at 37° C. After removing said sample, the plate was washed three times with washing solution.

Next, 100 µl of secondary antibody (biotinated sheep anti-mouse immunoglobulin, Amersham, diluted 500 times) were added to each well followed by incubation for 1 hour at 37° C. After removing the supernatant, the plate was washed three times with washing solution. Next, 100 µl of alkaline phosphatase labelled avidin (Dakopatts) were added to each well followed by incubation for 30 minutes at 37° C. The supernatant was removed from each of the wells and the plate was washed three times with washing solution. Next, 100 µl of enzyme substrate (p-nitro-phenylphosphate disodium salt (PNPP) dissolved in 10 mM diethanolamine buffer (pH 9.5), containing 0.5 mM $MgCl_2$, at a concentration of 100 mg/100 ml) were added to each well followed by allowing to stand for roughly 20 minutes at room temperature. Next, after stopping the reaction by the addition of 50 µl per well of reaction stopping solution (3N NaOH), the absorbance of each well was measured at 405 nm using an automated absorbance measuring device.

After bleeding the sensitized mice, the serum was separated from the whole blood and freeze-dried as the assay control serum. The spleens were immediately extracted using a sterile procedure from the bled mice by making an incision into the abdominal cavity. The extracted spleens were then placed in a container filled with RPMI-1640. The following procedure was performed at a sterile workbench. After washing the extracted spleens twice with RPMI-1640 medium and cutting away any adhered fatty tissue fragments, the spleens were vertically cut into two sections with a scissors and then finely dispersed in culture medium with a tweezers. The cell suspension was filtered with an autoclaved sieve or nylon cloth and collected. After removing the supernatant following centrifuging the cell suspension at low speed (800 rpm for 3 minutes), and dispersing the packed cells that formed as a precipitate by tapping, the cells were re-suspended with cold hemocytocatheresis solution (a mixture of 0.83% $NH_4Cl$ and Tris-HCl (pH 7.65) at a ratio of 9:1). After gathering the cells by low-speed centrifugation and washing once with RPMI-1640 medium, the number of cells were counted after re-suspending in RPMI-1640 medium.

On the other hand, after centrifuging fresh myeloma cells, ($P_3$-X63-Ag8-$U_1$)($P_3U_1$) rapidly propagated for 2–3 days in GIT medium (Nippon Seiyaku), at low speed (1000 rpm for 3 minutes) using round-bottom centrifuge tubes, removing the supernatant, and dispersing the packed cells that formed as precipitate by tapping, the number of cells were counted after suspending in RPMI-1640 (heated to 37° C.) base medium.

After fractioning the myeloma strain $P_3U_1$ cells, suspended in RPMI-1640 medium in advance, and spleen cells into round-bottom tubes for cell fusion in a proportion of roughly 1:5 in terms of the calculated number of cells, centrifuging at low speed and removing the supernatant, the packed cells that formed as a precipitate were dispersed by tapping. A solution, in which polyethylene glycol (PEG) at a temperature of 50° C. or less after autoclaving was previously dissolved in an equal volume of RPMI-1640 media, was slowly distributed among the tubes and mixed with the dispersed cells over the course of roughly 20–30 seconds while maintaining the temperature at 37° C. Next, after gently shaking the tubes for 1–2 seconds, the tubes were centrifuged for 15 seconds at 1100 rpm at a temperature of 25°–37° C.

Next, the solutions were mixed with a pipette while gradually adding 7 ml of RPMI-1640 medium at a temperature of 37° C.

Next, after removing the supernatant by centrifuging for 3 minutes at 800 rpm at a temperature of 25°–37° C., and re-suspending the packed cells while gradually adding 10 ml of HT medium, the cells were washed using a similar procedure. The cells were then re-suspended using HT medium (RPMI-1640 containing thymidine, hypoxanthine, and 10% fetal calf serum) so that the calculated number of myeloma cells was $1 \times 10^6$ cells/ml. This cell suspension was then distributed into a 96-well microplate for cell culturing, placing 0.1 ml in each well, followed by culturing in a $CO_2$ incubator ($CO_2$ concentration: 5%, 37° C.).

50 µl of HAT medium (RPMI-1640 medium containing hypoxanthine, aminopterin, thymidine, and 10% fetal calf serum) were then added to each well on the 2nd day of cell culturing. Moreover, the medium was replaced every 3 days using 10 µl of HAT medium per well. The degree of propagation of the hybridoma colonies was observed microscopically 2 weeks later. The antibody titers were measured in the same manner as titer measurement of serum antibodies by ELISA for the replaced culture supernatants of wells in which hybridoma colonies were confirmed at that time. Those cells in which production of the desired antibody was confirmed were transferred to a T-flask for large-scale propagation by sequentially transferring 1 ml per well until a final volume of 10 ml was reached using GIT medium after changing the culture liquid from HAT medium to HT medium in order to propagate the cells. Those cells were then placed in frozen storage as quickly as possible.

The thymuses of female mice (BALB/c, 4 weeks old) were extracted and suspended in GIT medium to which HT had been added ($5 \times 10^6$ cells/ml). The hybridomas were then ultradiluted using these thymus cells (5 cells/0.1 ml/well, 2.5 cells/0.1 ml/well, 1.25 cells/0.1 ml/well and 0.625 cells/0.1 ml/well). After culturing for 10 days to 2 weeks in a $CO_2$ incubator (5% $CO_2$, 37° C.), the degree of cell propagation and the antibody titer of the culture supernatant were measured. Re-cloning of the cells, subculturing, and frozen storage were performed as necessary. Frozen storage was performed as described below. The cultured cells were centrifuged (1000 rpm, 15°–25° C., 3 minutes) and the supernatant was removed. After dispersing the packed cells that formed as precipitate by gently tapping the tube, the cells were re-suspended ($5 \times 10^6$ cells/ml) by adding cold frozen storage medium (4° C.). 1 ml each of cell suspension was fractioned into 1.8 ml freezing tubes. After allowing the tubes to stand for at least one night at −80° C., the cells were placed in liquid nitrogen at a temperature of −194° C. and stored in the case of long-term storage.

10 positive hybridomas were obtained in this manner.

Next, the subclasses of antibodies contained in the culture supernatant from GIT medium of these hybridomas were determined by ELISA. In other words, 100 µl of cell culture supernatant were directly added to each well of a Cobind plate, the plate was incubated for 1 hour at 37° C., the supernatant was removed, and the plate was washed three times with washing solution. Next, 150 µl of blocking solution was added to each well, the plate was again incubated for 30 minutes at 37° C., the liquid was removed, and the plate was then washed three times with washing solution. Next, 100 µl of biotinated, goat-originating specific antibodies (Amersham) to each class, subclass, and type of mouse immunoglobulin were added to each well followed by incubation of the plate for 60 minutes at 37° C., removal of the liquid, and washing of the plate three times with washing solution.

Next, 100 µl of alkaline phosphatase-labelled avidin were added to each well, the plate was incubated for 30 minutes at 37° C., the supernatant was removed, and the plate was washed three times with washing solution. After adding 100 µl of PNPP enzyme substrate to each well and allowing the plate to stand at room temperature for roughly 20 minutes to allow suitable color development, the reaction was stopped by the addition of 50 µl of reaction stopping solution to each well. The absorbances of each well were then measured at 405 nm using an automated absorbance measuring device. As a result, all of the antibodies were determined to be IgG1-κ.

Next, hybridomas were selected that produced monoclonal antibodies that quantitatively bind with both ouabain and digoxin by antibody capturing using ELISA. Firstly, digoxin antigen was dissolved in a small amount of 60% ethanol. Next, this was diluted to a concentration of 0.01 mg/ml with coating solution (0.1M carbonate buffer, pH 9.5). 0.10 ml of that solution were distributed into each well of a flat-bottomed 95 well plate and allowed to stand overnight at 4° C.

Next, after removing the antigen solution, the plate was washed three times with washing solution. After adding 0.15 ml of blocking solution to each well, incubating for 30 minutes at 37° C., and removing the blocking solution, the plate was washed three times with washing solution resulting in the digoxinadsorbed plate.

On the other hand, antigen digoxin and ouabain were allowed to react separately for 30 minutes to 1 hour at 37° C. in the hybridoma culture supernatant containing the test monoclonal antibody, after which 0.10 ml of this reaction solution were added to each well followed by incubation for 1 hour at 37° C. This liquid was then removed and the plate was washed three times with washing solution. Next, 0.10 ml of biotitreated secondary antibody (anti-mouse Ig antibody diluted 500 times) was distributed into each well followed by incubation for 1 hour at 37° C. After removing the reaction solution, the plate was washed three times with washing solution. Next, 0.10 ml of alkaline phosphatase-labelled avidin (Dakopatts Ltd., D365 diluted 500 times) was distributed into each well followed by incubation of the plate for 30 minutes at 37° C. and washing three times with washing solution.

Next, 0.10 ml of enzyme substrate (in which 100 mg of p-nitrophenyl phosphate disodium salt (PNPP) was dissolved in 100 ml of 10 mM diethanolamine buffer (pH 9.5) containing 0.5 mM $MgCl_2$) was added to each well and allowed to stand at room temperature. When color had developed to a suitable extent (normally 20 minutes), 0.05 ml of reaction stopping solution (3N NaOH) was added to each well followed by measurement of absorbance at 405–410 nm using an automated absorbance measuring device.

As a result, it was discovered that the two hybridomas of 249F8 and 278A9 quantitatively reacted with both ouabain and digoxin, and those hybridomas were used in later experiments. The results of the above-mentioned ELISA antibody capturing for hybridomas 249F8 and 278A9 are indicated in FIG. 2.

Furthermore, hybridoma 249F8 was named mouse hybridoma cell line SBM 319 and was entrusted to the Fermentation Research Institute of the Agency of Industrial Science and Technology on Dec. 12, 1990 as Fermentation Research Institute Deposit No. 3197 (FERM BP-3197), while hybridoma 278A9 was named mouse hybridoma cell line SBM 320 and was also entrusted on Dec. 12, 1990 as Fermentation Research Institute Deposit No. 3198 (FERM BP-3198).

Example 3: Production of Monoclonal Antibody by In Vivo Culturing

Hybridomas 249F8 and 278A9 were cultured in GIT medium to prepare cell suspensions of $10^7$ cells/ml after washing with RPMI-1640 BASE medium. 0.5 ml per mouse of pristane were intraperitoneally injected into 5–6 week old female BALB/c mice followed by intraperitoneal injection of 0.5 ml of the above-mentioned hybridoma cell suspension two weeks later. As ascites accumulated in roughly 1–10 days causing hypertrophy of the abdomen, it was removed with a syringe. 5–10 ml of ascites were obtained per mouse in this manner.

This ascites was separated by centrifugation for 10 minutes at 4° C. and 3000 rpm, and the supernatant was collected. The supernatant was salted out by addition of an equal volume of saturated ammonium sulfate solution (adjusted to pH 7.4 with ammonia water). This mixture was then separated by centrifugation for 30 minutes at 4° C. and 14,000 rpm (1,000×G) and the supernatant was removed. The precipitate was dissolved in a suitable amount of physiological saline and the residual ammonium sulfate was removed either by dialyzing this solution with physiological saline, or fractionating with a Sephadex G25 M column. Removal of ammonium sulfate was confirmed by using Nessler's reagent. Next, after removing any fat using cold clarificant (Friegen), the amount of protein was measured, the solution was either provided for following experiments as unrefined antibody fraction sample, or placed in frozen storage.

Next, the antibody was purified by protein G-Sepharose column chromatography. A column filled with protein G-Sepharose was washed with 20 bed volumes of binding buffer (Affi-Gel Protein AMAPS II buffer, Bio-Rad, 153-6160, pH 9.0). Unrefined antibody fraction sample containing roughly 5 mg/ml of IgG was mixed in a 1:1 ratio with the above-mentioned binding buffer and applied on the above-mentioned column followed by washing the column with 15 bed volumes of binding buffer.

Next, the IgG fraction was eluted with 10 bed volumes of elution buffer (having the same composition as the binding buffer adjusted to pH 3.0). At this time, 8 ml of 1M Tris-HCl buffer per 25 ml of eluent were placed in the receiving vessel in advance to neutralize the pH of the eluent in the neutral range. The medium of the collected antibody fraction was replaced with physiological saline by ultrafiltration using a molecular sieve (M.W.: 30,000). The protein concentration of the resulting antibody solution was measured, and after adjusting to a suitable protein concentration, the solution was freeze-dried and stored for use in later experiments.

Example 4: Determination of Characteristics of Monoclonal Antibody

A. Measurement of Antibody Titer by ELISA

When the monoclonal antibody titer was measured by the ELISA method described in Example 1, the titer of monoclonal antibody 249F8 (monoclonal antibody produced from hybridoma 249F8) was 4,300 units/mg, and the titer of monoclonal antibody 278A9 (monoclonal antibody produced from hybridoma 289A9) was 2,200 units/mg.

B. Monoclonal Antibody Cross-Reactivity

The cross-reactivity of monoclonal antibodies 249F8 and 278A9 of the present invention, as well as rabbit polyclonal antiserum R49, with respect to various substances (antigens) was tested using the ELISA antibody capturing method described in Example 2. The substances indicated in the following Table 1 were used as antigens in this testing.

Table 1

(1) Cardiac Glycosides (cis-trans-cis forms)
  1. Ouabain (ouabagenin-mono-rhamnoside)
  2. Digoxin (digoxigenin-tri-digitoxoside)
  3. Digoxigenin-bis-digitoxinoside
  4. Digitoxin (digitoxigenin-tri-digitoxoside)
  5. Digitoxigenin-mono-digitoxoside
  6. Digitoxigenin-bis-digitoxoside
  7. Digiproside (digitoxigenin-mono-fucoside)
  8. Strospeside (digitoxigenin-mono-digitaloside)
  9. Cymarine (strophanthidin-mono-cymaroside)
  10. Helveticoside (strophanthidin-mono-digitaloside)
  11. Convallatoxin (strophanthidin-mono-rhamnoside)
(2) Cardiac Glycosides having Oxidized Sugar Portions (cis-trans-cis forms)
  12. Ouabain-oxide
(3) Cardiac glycoside genins (cis-trans-cis forms)
  13. Ouabagenin
  14. Strophanthidin
  15. Digoxigenin
  16. Digitoxigenin
  17. Bufalin (trans-trans-cis form)
  18. Uzarigenin (4) Steroid Hormones (trans-trans-trans forms)
19. Androsterone
20. β-Estradiol
21. 5-Pregnen-3β-20-one
22. Progesterone
23. Hydrocortisone
24. d-Aldosterone
25. Corticosterone
(5) Steroids (trans-trans-trans forms)
26. Cholesterol
(6) Bile Acids (cis-trans-trans forms)
27. Cholic acid
(7) Unsaturated Fatty Acids
28. Arachidonic acid
29. Linoleic acid
(8) Phospholipids
30. PAF (L-d-phosphatidylcholine-β-aceyl-γ-O-hexadecyl)
31. LysoPAF (L-α-lysophosphatidylcholine-γ-O-hexadecyl)
(9) Sugars
32. L-Rhamnose
33. D-Digitoxose
34. D-Fucose
(10) Steroid Sapogenins (trans-trans-trans forms)
35. Diosgenin
(11) Unsaturated Lactones and their Derivatives
36. 2(5H)-Furanone
37. 2-Cyclopentene-1-one
38. γ-Butylolactone
39. 2,3-Dihydrofuranone
(12) Other Derivatives of Cardiac Glycosides
40. Cyclohexane
41. Cyclohexanol
42. cis-2-Methylcyclohexanol
43. cis-Hydrindane
44. trans-Hydrindane
(13) Substance for Reconfirming Cross Reactivity
45. Ouabain-BSA
(14) Sodium Ion Concentration Antagonist Type
46. SPAI-1

Furthermore, the indication of "trans-trans-cis", etc. shown after the types of substances indicates the sequence of the type of bonding of the A- and B-rings, the B- and C-rings and the C- and D-rings within the steroid structure according to their cis- and trans-configurations.

Figure 3A:
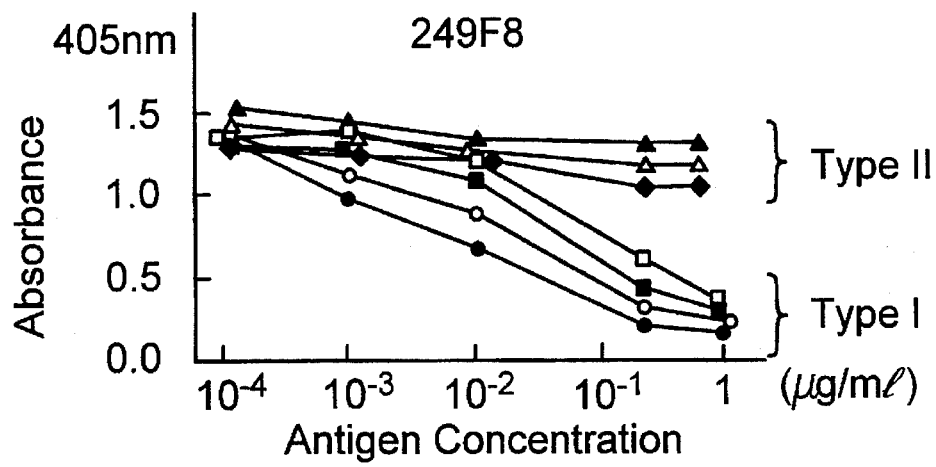
FIGS 3(A) and 3(B) gives graphs indicating the cross-reactivity of monoclonal antibodies 249F8 (FIG. 3A) and 278A9 (FIG. 3B) of the present invention with various cardiac glycosides and their aglycons.
Figure 3B:
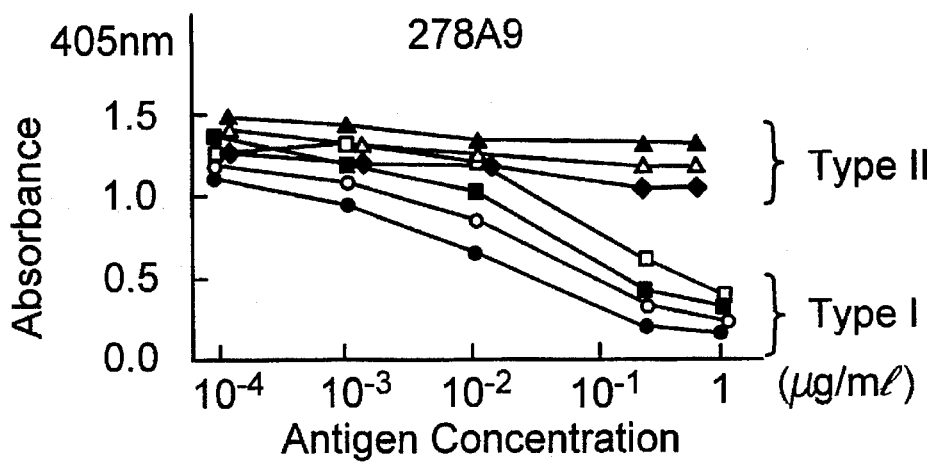

A portion of the results of the above-mentioned testing is subsequently described in Table 3. Moreover, those results are also indicated in FIG. 3. As a result of this testing, it was discovered that both of the two types of monoclonal antibodies of the present invention have steroid structures, and those antibodies specifically react only with substances in which the bonding between the C- and D-rings is of the "cis" type.

C. Correlation Between Reactivity of Various Substances with respect to Monoclonal Antibodies and $Na^+,K^+$-ATPase Inhibitory Activity It is known that ouabain inhibits the enzyme activity of $Na^+,K^+$-ATPase. As such the $Na^+,K^+$-ATPase inhibitory activity of the various substances used as antigens in Example 4, Part B was examined to investigate the correlation between that inhibitory activity and reactivity with the monoclonal antibody of the present invention.

1.35 ml of TES buffer (80 mM TES, 200 mM NaCl, 9 mM $MgSO_4.7H_2O$ and 10 mM EGTA adjusted to pH 7.4 with NaOH), 0.27 ml of 0.2% ODG (octyl-D-glucoside), 0.27 ml of $10^{-5}$M sample ($10^{-6}$M during reaction), and 0.44 ml of distilled water were added to a plastic test tube which was then placed in an incubator at 25° C. 0.27 ml of 1 mM or 100 mM KCl and 50 μl of ATPase solution (stock solution, in which 5 units of $K^+,K^+$-ATPase (Sigma) were dissolved in 2 ml of 10 mM TES (pH 7.4) diluted 2.5 times with 10 mM TES (pH 7.4) as necessary) were added followed by incubation for 5–10 minutes at 25° C. Next, the reaction was started by addition of 50 μl of ATP solution (71 mg of ATP dissolved in 5 ml of 10 mM TES (pH 7.4) (Sigma)).

The reaction was allowed to proceed at 25° C. for 30 minutes in the case of using 1 mM KCl (0.1 mM in the reaction solution), and for 10 minutes in the case of using 100 mM KCl (10 mM in the reaction solution). Next, 0.03 ml of 1% Trion X-100 solution (in distilled water) and 0.3 ml of 2.5% A mM solution (5 g of $(NH_4)_6Mo_7O_{24}.4H_2O$ dissolved in 6N $H_2SO_4$ and brought to a volume of 200 ml) were mixed immediately prior to use (for a total of 0.33 ml) and then added to the reaction solution followed by incubation for 10 minutes at 25° C. to stop the reaction and develop color. The absorbance of the reaction solution was then measured at 660 nm and the $Na^+,K^+$-ATPase inhibition rate (%) was calculated according to the following formula.

$Na^+,K^+$-ATPase Inhibition Rate $(\%)=[(A_o-A_w)/A_o]\times 100$ $A_o$: $Na^+,K^+$-ATPase activity when sample not added $A_w$: $Na^+,K^+$-ATPase activity when sample added As a result of the above-mentioned measurement, the results indicated in Table 2 were obtained.

TABLE 2

| Test Substance | ($Na^+$, $K^+$-ATPase Inhibition) Rate (%) | |
| --- | --- | --- |
| | 0.1 mM $K^+$ | 10 mM $K^+$ |
| Ouabain | 41 | 18 |
| Digoxin | 45 | 18 |
| Digitoxin | 41 | 11 |
| Ouabagenin | 44 | 6 |
| Digoxigenin | 44 | 12 |
| Digitoxigenin | 44 | 17 |
| Uzarigenin | 42 | 6 |
| Progesterone | 3 | 5 |
| Hydrocortisone | −3 | −1 |
| α-Aldosterone | 1 | −11 |
| Corticosterone | −4 | 1 |
| Cholic acid | 2 | −3 |
| Arachidonic acid | −5 | −2 |
| Linoleic acid | −7 | −5 |
| PAF | −3 | 1 |
| LisoPAF | −2 | 0.4 |
| L-Rhamnose | −2 | −4 |
| 2(5H)-Furanone | 6 | −5 |
| Cyclohexanol | −3 | 0.4 |
| cis-2-Methylcyclohexanol | −2 | 2 |
| cis-Hydrindane | −1 | 0.5 |
| SPAI-1 | −3 | 4 |

SPAI-1: Refer to Araki, K. et al. (1989), Biochem. Biophys. Res. Commun. 64(1), 496–502.

The relationship between the above-mentioned cross-reactivity, the $Na^+,K^+$-ATPase inhibitory activity indicated in the above-mentioned Table 2, and presence of a C-D ring cis-bonding structure within the test substances is indicated in Table 3 below.

TABLE 3

| Test Substance | Ouabailike Na+,K+-ATPase Inhibitory Activity | Cross Reactivity with Monoclonal Antibody | Presence of C-D Ring cis Bonding Structure |
| --- | --- | --- | --- |
| Ouabain | + | + | + |
| Digoxin | + | + | + |
| Digitoxin | + | + | + |
| Ouabagenin | + | + | + |
| Digoxigenin | + | + | + |
| Digitoxigenin | + | + | + |
| Uzarigenin | + | + | + |
| Progesterone | − | − | − |
| Hydrocortisone | − | − | − |
| α-Aldosterone | − | − | − |
| Corticosterone | − | − | − |
| Cholic acid | − | − | − |
| Arachidonic acid | − | − | − |
| Linoleic acid | − | − | − |
| PAF | − | − | − |
| LisoPAF | − | − | − |
| L-Rhamnose | − | − | − |
| 2(5H)-Furanone | − | − | − |
| Cyclohexanol | − | − | − |
| cis-2-Methyl-cyclohexanol | − | − | − |
| cis-Hydrindane | − | − | − |
| SPAI-1 | − | − | − |

As can be seen from the table above, monoclonal antibodies 249F8 and 278A9 of the present invention have common properties. As is clear from these results, those substances that react with the monoclonal antibodies of the present invention have Na+,K+-ATPase inhibitory activity. In other words, it became clear that those substances that react with the monoclonal antibodies of the present invention, and those substances that have potassium ion concentration antagonist type Na+,K+-ATPase inhibitory activity have a common structural portion comprised of a cis-bonded D-ring and its accompanying substitution groups.

Example 5: Quantitative Determination of Cardiac Glycoside by Scintillation Proximity Assay Using the Monoclonal Antibody of the Present Invention The following describes the principle of scintillation proximity assay (SPA). After labelling an antigen identical to the test antigen with a radioisotope, an antibody (primary antibody) is reacted with said antigen. Another antibody to said primary antibody (secondary antibody) and a fluorescent substance are bonded to a solid carrier and this antibody carrier is allowed to react with the reaction product of the above-mentioned primary antibody and labelled antigen. As a result, the above-mentioned primary antibody bonds to the secondary antibody on the solid carrier, which in turn results in the fluorescent substance bonded on the solid carrier being brought in close proximity to the labelled antigen bound to the primary antibody. The fluorescent substance is affected by the radioisotope label causing the fluorescent substance to fluoresce. Thus, measuring the intensity of this fluorescence allows the amount of labelled antigen that reacted with the primary antibody to be determined. In the above-mentioned reaction, if the labelled antigen is present together with the test antigen identical to it, the two antigens mutually compete for the primary antibody. Consequently, the test antigen inhibits the reaction between the labelled antigen and the primary antibody. As a result, the amount of test antigen can be measured by measuring the intensity of the fluorescence.

0.1 ml of 50 mM Tris-HCl buffer (pH 7.4, containing 0.9% NaCl and 0.01% Triton X-100), 0.1 ml of primary antibody solution (monoclonal antibody 249F8 or 278A9 dissolved in Tris-HCl buffer to a protein concentration of 0.001 mg/ml), 0.1 ml of labelled antigen solution (250 μCi/250 μl of [21,22-$^3$H]ouabain (Amersham) in toluene/ethanol (1:9) diluted 1000 times when used), and 1 ml of sample or labelled antigen (ouabain or digoxin dissolved in distilled water to concentrations of $10^{-4}$, $10^{-5}$, $10^{-6}$, $10^{-7}$ and $10^{-8}$M) were placed in an RIA assay tubes and stirred. After addition of 0.1 ml of SPA anti-mouse Ig reagent and stirring adequately to form a uniform suspension, the tubes were incubated for 20 hours at room temperature while shaking.

The amount of radioisotope bonded to the small spheres was measured with a β-scintillation counter. The relationship between the concentration of ouabain or digoxin and radioactivity in this case is indicated in FIG. 4.

The detectable ranges in the case of performing the above-mentioned measurement using the monoclonal antibodies of the present invention are indicated in Table 4. Furthermore, the detectable ranges in the case of performing ELISA antibody capture using the monoclonal antibodies of the present invention are also shown in Table 4.

TABLE 4

| Monoclonal Antibody | Test Antigen | RIA | ELISA |
| --- | --- | --- | --- |
| 249F8 | Ouabain | $2 \times 10^{-7} - 2 \times 10^{-9}$M | $2 \times 10^{-7} - 6.8 \times 10^{-9}$M |
|  | Digoxin | $2 \times 10^{-6} - 2 \times 10^{-8}$M | $2 \times 10^{-7} - 1.2 \times 10^{-9}$M |
| 278A9 | Ouabain | $2 \times 10^{-7} - 2 \times 10^{-9}$M | $2 \times 10^{-7} - 6.8 \times 10^{-9}$M |
|  | Digoxin | $2 \times 10^{-6} - 2 \times 10^{-8}$M | $2 \times 10^{-7} - 1.2 \times 10^{-9}$M |

Example 6: Blocking of Ouabain Na+, K+, ATPase Inhibition by Anti-Ouabain Antibody The effect of addition of anti-ouabain antibody to ouabain solution on reduced inhibition of Na+,K+-ATPase by ouabain was measured according to the method of Youngberg and Youngberg.

Figure 7:
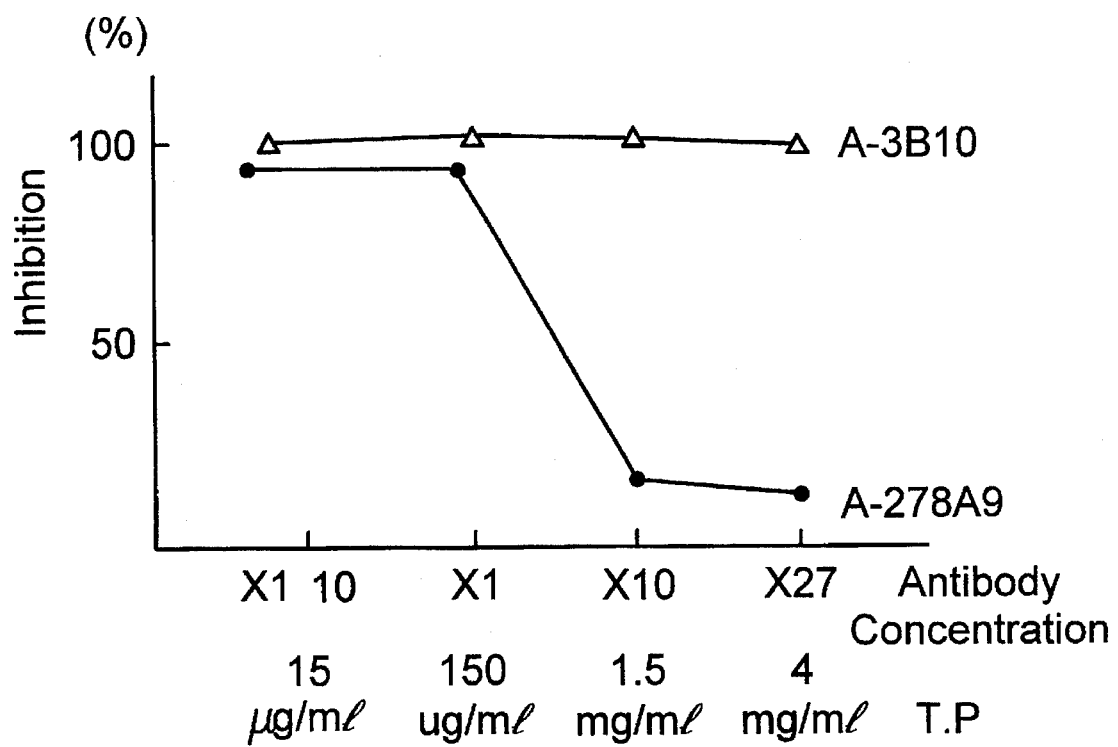
FIG. 7 is a graph indicating the neutralizing effects on $Na^+,K^+$-ATPase activity inhibitory action of monoclonal antibodies of the present invention.

A suitable amount of ouabain and antibody (278A9 or 3B10) were reacted for 1 hour at 37° C. Following completion of the reaction, the solution was deproteinized with centricon 30 (molecular weight 30,000 cutoff filter). Next, the ouabain activity of this deproteinized solution was measured according to the above-mentioned method of Youngberg and Youngberg. Those results are indicated in FIG. 7.

Although anti-ouabain antibody 278A9 blocked the Na+, K+-ATPase inhibitory action of ouabain at a protein concentration of 1.5 mg/ml or more, anti-TNF antibody 3B10 did not block this action over the same concentration range. Thus, it was clear that anti-ouabain antibody 278A9 recognizes the active sites of the molecular structure of ouabain that bring about Na+, K+-ATPase inhibitory action.

Furthermore, measurement of Na+,K+-ATPase activity according to the method of Youngberg and Youngberg was performed as described below.

100 μl of buffer (60 mM Tris-HCl (pH 7.2), 220 mM NaCl, 0.2 mM KCl, 1 mM EGTA and 8 mM MgCl$_2$), 40 μl of sample, 40 μl of ATPase solution (50 mM Tris-HCl (pH 7.2) in which 5 units 12 ml of ATPase was diluted 22.5 times with 50 mM Tris-HCl (pH 7.2)), and 40 μl of ATP solution (50 mM Tris-HCl (pH 7.2) containing 10 mM ATP) were placed in the wells of an assay plate and allowed to react for 30 minutes at room temperature.

Next, 50 μl of ammonium molybdate sulfuric acid solution (14% (v/v) ammonium molybdate dissolved in sulfuric acid) were added to each well to stop the reaction. Next, 50 μl of stannous chloride hydrochloric acid solution (2 g of $SnCl_2.2H_2O$ dissolved in 5 ml concentrated hydrochloric acid followed by dilution by a factor of 200 with distilled water) were added to each well after which 2–5 minutes were allowed for reduction of the molybdate. As such, inorganic phosphorous produced by $Na^+,K^+$-ATPase was formed as molybdate and reduction of this molybdate produces a blue color, the absorbance of which was measured at 690 nm.

Figure 8:
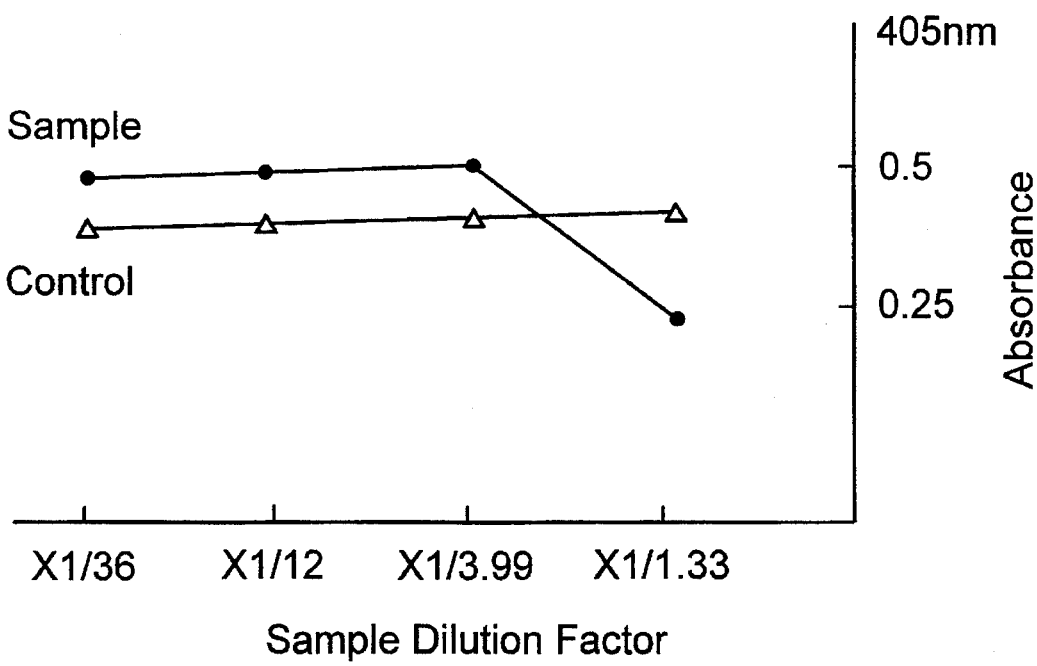
FIG. 8 is a graph indicating the relationship between absorbance and the concentration of HPLC-purified, human plasma OLF fraction as measured by ELISA using a monoclonal antibody of the present invention.

Example 7: Measurement of Human Plasma OLF (OuabaiLike Factor) Fraction Purified by HPLC by ELISA Using Anti-Ouabain Antibody Human plasma purified by HPLC (315 ml of plasma) was dissolved in 50 μl of ethanol followed by the addition of 380 μl of distilled water to bring to a total volume of 430 pl. 30 μl of 0.1% gelatin-PBS(−) were added to 90 μl of this sample followed by suitable dilution. This was allowed to react with anti-ouabain 278A9 for 1 hour at 37° C. 100 μl/well of the above-mentioned reaction mixture was distributed into a digoxicoated assay plate followed by reaction for 1 hour at 37° C. As a result, the biotitreated secondary antibody (anti-mouse Ig), alkaline phosphatase-labelled avidin and substrate p-nitrophenyl-phosphate (PNPP) reacted sequentially with 278A9 bonded to digoxin on the plate, after which the absorbance of the mixture was measured at 405 nm. Those results are indicated in FIG. 8.

Reaction between the sample and anti-ouabain antibody 278A9 was observed at a high sample concentration of a roughly ⅓ dilution or more. Thus, it was verified that a substance is present in HPLC purified human plasma that reacts with anti-ouabain antibody.

Based on these results, it was verified that 278A9 can also be used in purification of OLF.

Example 8: Comparison of the Immunocapturing (ELISA) Method of the Present Invention and Official Testing In order to compare the immunocapturing (ELISA) method using the antibody of the present invention with the official testing method, various cardiac glycosides were measured according to these methods. Digoxin (Sigma Chemical Co., Code No. D-6003) was used for the standard substance, and digoxin tablets (Sando Pharmaceutical, Lot No. 7271), digoxin injection preparation (Chugai Pharmaceutical, Lot No. BOL01), Deslanoside injection solution [Digilanogen C. injection solution, (Fujisawa Pharmaceutical Co. (abbreviated as Company F), Lot No. 1560), Deslanoside injection (Kobayashi Kako (abbreviated as Company K), Lot No. Y020), Cediland injection solution (Sando Pharmaceutical (abbreviated as Company S), Lot No. 7303)]and Resibufogenin injection solution (Taisho Pharmaceutical, Lot No. 0198P) were used for the test samples.

The standard solution and test solutions were prepared from the above-mentioned samples in the manner described below. The standard solution for official testing and measurement of extracted reagents was prepared by accurately weighing 25.0 mg of standard digoxin, dissolving in 50 mg of warm ethanol followed by cooling, and finally adding ethanol to accurately bring to a final volume of 100 ml. 10 ml of this solution was then accurately measured followed by the addition of ehtanol to accurately bring to a final volume of 100 ml. Thus, the concentration of the standard solution prepared in this manner was 2.5 mg/100 ml. The standard for measurement of noextracted samples was prepared by diluting a 60% aqueous ethanol solution of digoxin (1 mg/ml) with water by a factor of 10. This was then diluted an additional 250 times with ELISA diluent (0.1% gelatin and 0.1% $NaN_3$ in D'-PSB(−)) to bring to a final concentration of 400 ng/ml.

The sample solution made from capsules was prepared as described below. Twenty or more capsules were weighed and formed into a powder. Next, an amount of powder equivalent to 2.5 mg of digoxin ($C_{41}H_{64}O_{14}$) was accurately weighed out followed by the addition of 5 ml of boiled n-propanol and vigorous stirring. Next, the solution was allowed to cool by standing while stirring occasionally for 20 minutes. The solution was transferred to a separatory funnel, and 20 ml of water were added followed by two extractions with 30 ml of chloroform/n-propanol mixture (5:1). The extracts were washed with 5 ml of water each time and filtered into a 100 ml volumetric flask using absorbent cotton soaked in chloroform. Ethanol was added to bring to a final volume of 100 ml resulting in the obtaining of the sample solution having a concentration of 2.5 mg/100 ml.

In order to prepare the sample solution for the official testing reagent from the injection solutions, an amount of injection solution equivalent to 2.5 mg of digoxin was accurately measured, and placed in a separatory funnel followed by the addition of water to bring to a volume of 50 ml. 1 ml of dilute sulfuric acid (addition of 5.7 ml of sulfuric acid to 10 ml of water followed by the addition of water to bring to a volume of 10 ml after cooling) was added followed by extraction with 35 ml, 30 ml and 30 ml of a chloroform/n-propanol mixture (5:1). Each of the extracts were washed with 5 ml of water. The extracts were then transferred into a 100 ml volumetric flask using absorbent cotton soaked in chloroform where they were combined followed by the addition of ethanol to bring to a final volume of 100 ml. The concentration of the resulting sample solution was 2.5 mg/100 ml.

The sample solution for ELISA from the injection solutions was obtained by diluting injection solution (250 μg/ml) 2.5 times with water to bring to a concentration of 100 μg/ml and diluting an additional 250 times with ELISA diluent (0.1% gelatin and 0.1% $NaN_3$ in D'-PBS(−)) to bring to a final concentration of 400 ng/ml.

Official testing was performed in the manner described below. 10 ml each of the standard solution and sample solutions prepared as described above were accurately measured and placed in separate Erlenmeyer flasks. These were evaporated nearly to dryness while feeding in air over a water bath. After allowing to stand for 15 minutes in a dessicator (reduced pressure, phosphorous pentoxide), the dried solids were dissolved by addition of 5 ml each of acidic ferric chloride reagent (1 ml of ferric chloride reagent, prepared by dissolving 9 g of ferric chloride in water and bringing to a volume of 100 ml, and 5 ml of sulfuric acid added to 10 ml of glacial acetic acid). The solutions were allowed to stand for 10 minutes shaded from light at a temperature of 30° C. or less while stirring occasionally. The solutions were filtered using glass fiber as necessary. The maximum absorbance values for the resulting solutions were determined by measuring the absorbance for 2 minutes at 590 nm using an Hitachi U-3200 spectrophotometer and acidic ferric chloride reagent as the control.

ELISA was performed in the manner described below. Digoxin serving as the standard antigen was dissolved in 60% ethanol to bring to a concentration of 1 mg/ml. This was additionally diluted with coating solution (1.59 mg of $Na_2CO_3$, 2.93 mg of $NaHCO_3$ and 0.20 mg of $NaN_3$ dissolved in 1,000 ml of distilled water: carbonate/bicarbonate 0.1M, pH 9.5) to bring to a concentration of 0.01 mg/ml. This was then fractioned into an assay plate (Serocluster flat-bottomed 96 well plate, Costar, Code No. 3590) placing 0.10 ml in each well. This plate was then sealed and allowed to stand overnight at 4° C.

On the other hand, suitable concentrations of antigen solution and antibody solution (monoclonal mouse $IgG_1$-κ anti-ouabain:MAaf278A9, final concentration: 0.8 µg/ml) were prepared using diluent (RIA grade gelatin (Bio Rad Ltd., 170–6537, Control M3354) in pH 7.5 D'PBS(−) (Nissui Ltd., RPN-05913)), 70 µg/well were distributed into a reaction plate 5 (Serocluster V-low 98-well, Costar Code No. 3897), and allowed to react for 30 minutes to 1 hour at 37° C.

Next, the antigen solution was removed from the assay plate after which the plate was washed three times with washing solution (PBS-T) (pH 7.4 D'PBS(−) containing 0.1% w/v Tween 20 (Bio Rad Ltd., 1706537) and 0.17% w/v $NAN_3$). Next, 0.15 ml/well of blocking solution (1% w/v gelatin in pH 7.4 D'-PBS(−) containing 0.1% w/v $NAN_3$) was added to the plate followed by incubation for 30 minutes at 37° C. The blocking solution was removed and the plate was washed three times with washing solution.

Next, 0.1 ml/well of solution previously allowed to react in the above-mentioned V-bottomed plate wells were added followed by incubation for 1 hour at 37° C. The reaction solution was removed and the plate was washed three times with washing solution. 0.10 ml/well of biotinated secondary antibody (sheep biotinated anti-mouse Ig total antibody (Amersham Ltd., RPN.1021, Lot 13) diluted 500 times) were added followed by incubation for 60 minutes at 37° C. The reaction solution was removed and the plate was washed three times with washing solution.

Next, 0.10 ml/well of alkaline phosphatase-labelled avidin (Dakopatts Ltd., D365, Lot 029, diluted 500 times) were added followed by incubation for 30 minutes at 37° C. The reaction solution was then removed and the plate was washed three times with washing solution. Next, enzyme substrate (PNPP, 100 mg of sodium p-nitrophenylphosphate salt dissolved in 10 ml of pH 9.5 10 mM diethanol amine buffer containing 0.5 mM $MgCl_2$) was fractioned into the plate and allowed to stand at room temperature. 0.05 mg/well of reaction stopping solution (aqueous 3N NaOH solution) were added when a suitable degree of color development was obtained (normally roughly 20 minutes).

Finally, the absorbance at 405–410 nm was measured using an automated absorbance measuring device (Micro ELISA Auto Reader MR 580, A Dynatech Product).

Figure 9A:
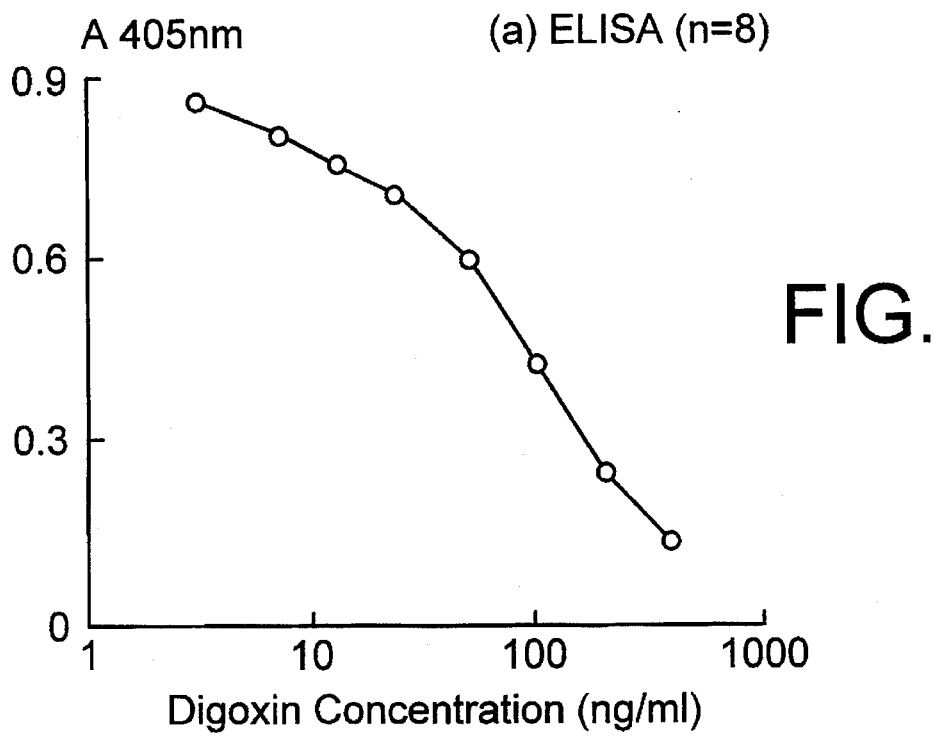
FIGS. 9(a) and 9(b) and 10 are graphs indicating the relationship between absorbance and digoxin concentration as measured by ELISA (antibody capture method, FIGS 9(a) and 10(a)) and the official measurement method (Keller-Kiliani method, FIG. 9(b) and 10(b)).
Figure 9B:
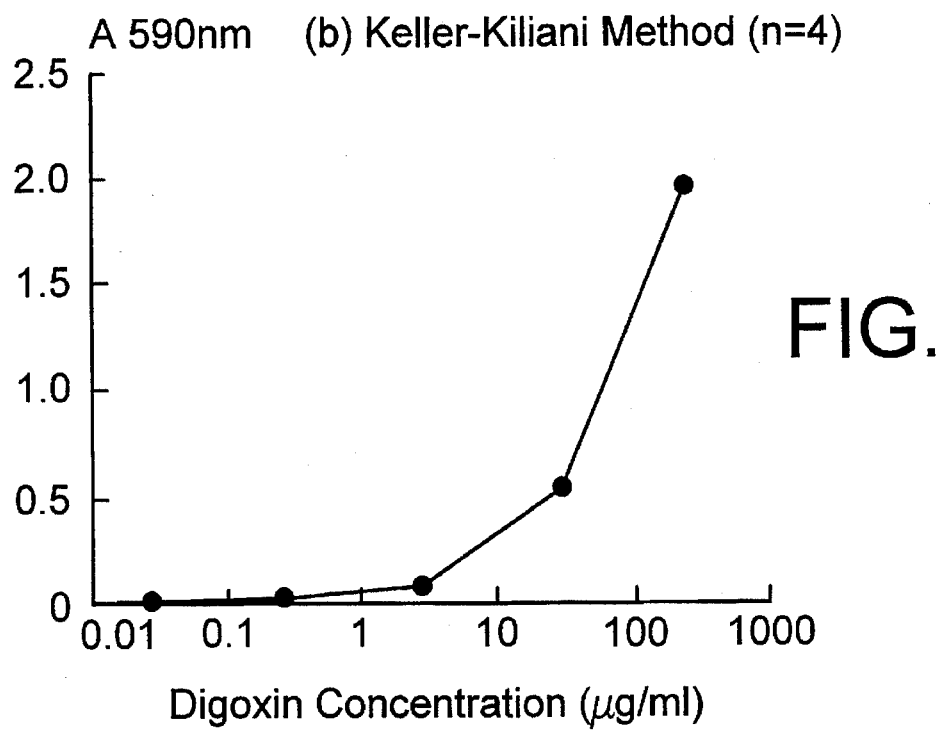
Figure 10:
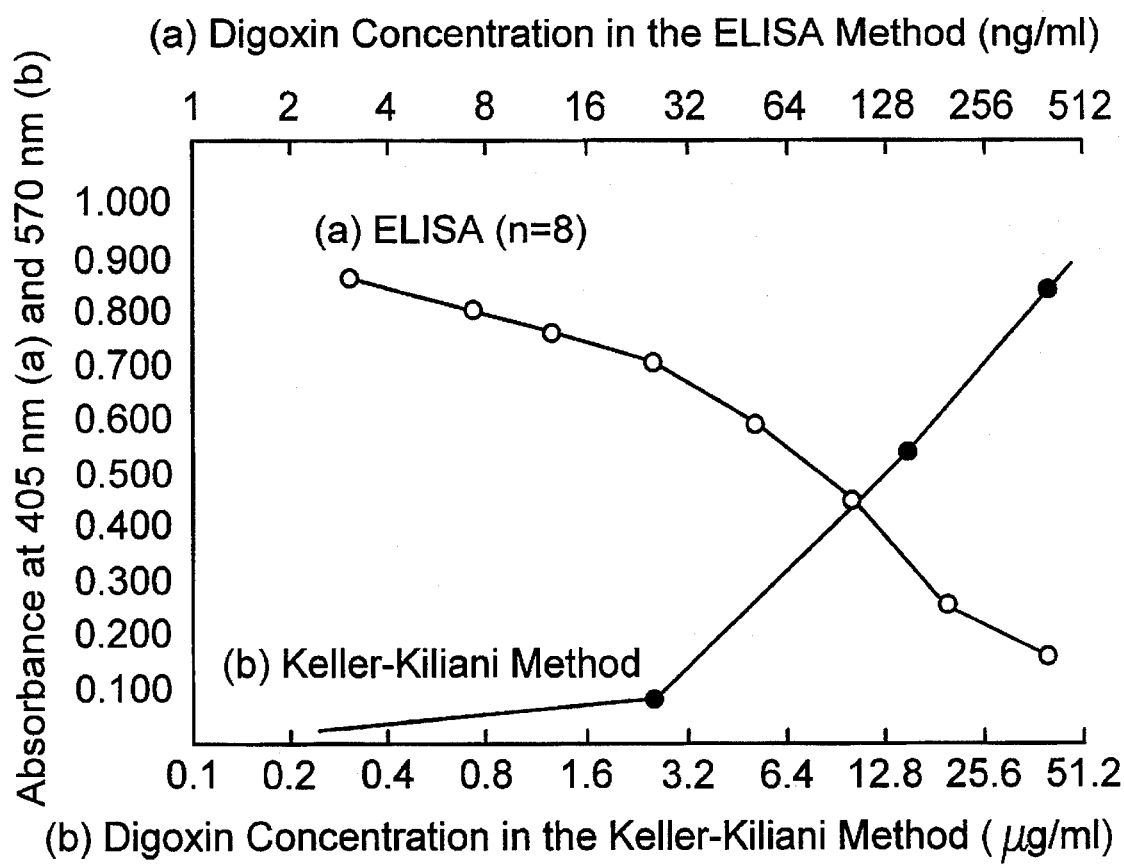

The above-mentioned results are indicated in FIG. 9 and FIG. 10. As can be understood from these results, the optimum concentration region for measurement using the official testing method is 3–30 µg/ml, while that for the ELISA method is 0.01–0.3 µg/ml, indicating that the detection sensitivity of the ELISA method is roughly 300 times greater than that of the official testing method. Thus, low concentration specimens can be quantitatively determined with a high degree of accuracy with the ELISA method using the monoclonal antibody of the present invention.

Figure 11:
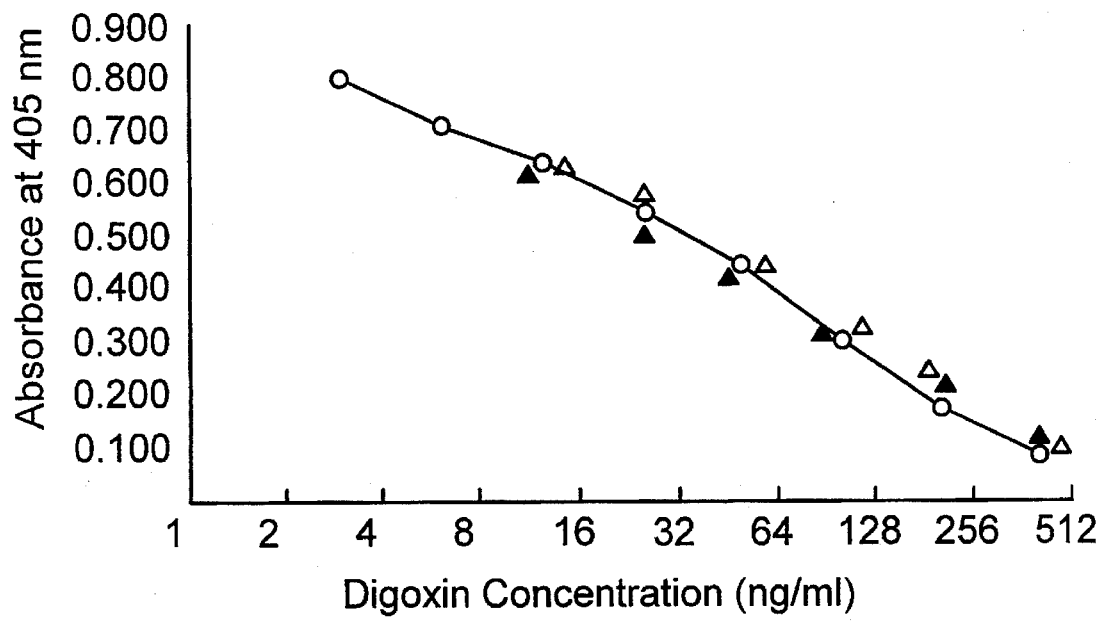
FIG. 11 is a graph indicating that measured values are in close agreement in the case of measuring injection preparation after direct dilution, and measuring digoxin after first extracting the digoxin.

The official testing method (Keller-Kiliani method) is a colorimetric method wherein the sugar chain portion of a cardiac glycoside is colored in the form of digitoxose by acidic ferric chloride reagent. Although in the official testing method it is necessary to separate the digoxin in advance by an extraction procedure, as is indicated in FIG. 11 and Table 5, in the case of measuring the digoxin of a digoxin injection preparation by ELISA, measurement can be performed directly while omitting the extraction procedure.

TABLE 5

Relationship Between Digoxin Measured Values in the Case of Measuring After Directly Diluting the Digoxin Injection Preparation, and in the Case of Measuring Following Extraction of Digoxin

|  | Indicated Value | Measured Value |
| --- | --- | --- |
| Digoxin content when digoxin injection preparation is diluted directly | 250 µg/ml | 252 ± 15 µg/ml (n = 5) |
| Digoxin content when digoxin injection preparation is extracted | 250 µg/ml | 249 ± 19 µg/ml (n = 5) |

The results of measuring digoxin tablets and digoxin injection solution by the official testing method (Keller-Kiliani method) and ELISA (antibody capturing method) are as indicated in the following table.

TABLE 6

| Measurement Method | Digoxin Content | | m.a./i.a. × 100 (%) |
| --- | --- | --- | --- |
|  | Indicated Amount (i.a.) | Measured Amount (m.a.) |  |
| Official method | 250 µg/tablet | 195 µg/tablet | 78% |
| ELISA | 250 µg/tablet | 190 µg/tablet | 76% |
| Official method | 250 µg/ampule | 255 µg/ampule | 102% |
| ELISA | 250 µg/ampule | 250 µg/ampule | 100% |

As is indicated above, there was good agreement between the values measured with the official testing method and those measured with ELISA for both tablets and injection preparations. Furthermore, the fact that the measured values in the case of tablets correspond to 76–78% of the indicated values is believed to reflect the extraction efficiency.

Figure 12:
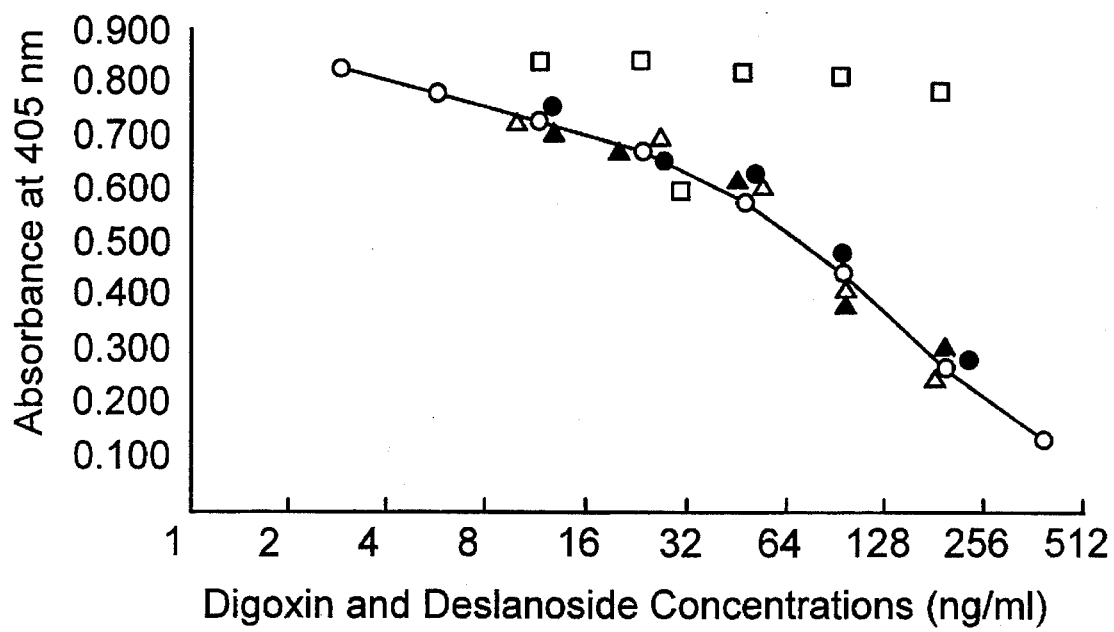
FIG. 12 is a graph indicating the results of measuring three types of deslanoside injection preparations and 1 type of regibufogenin by ELISA.

As it was verified that digoxin injection preparations can be measured using the ELISA method without requiring an extraction procedure, quantitative determination was performed for three other cardiac glycoside deslanoside injection preparations. Those results are indicated in FIG. 12 and Table 7.

TABLE 7

Concentration of Cardiac Glycoside Contained in Digoxin and Deslanoside Injection Preparations by ELISA Using the Monoclonal Antibody of the Present Invention

| Injection Preparation | Indicated Value | Measured Value |
| --- | --- | --- |
| Digoxin injection preparation | 250 µg/ml | 252 ± 15 µg/ml (n = 5) |
| Deslanoside injection preparation (Company F) | 200 µg/ml | 196 ± 18 µg/ml (n = 5) |
| Deslanoside injection preparation (Company K) | 200 µg/ml | 198 ± 28 µg/ml (n = 5) |
| Deslanoside injection preparation (Company S) | 200 µg/ml | 198 ± 24 µg/ml (n = 5) |

As can be understood from these results, measured values were obtained as indicated for all samples. On the other hand, although quantitative determination of Resibufogenin (which does not contain sugar) was attempted, as the optimum measuring concentration shifted upward, it was verified that the ELISA method allows specific quantitative determination ouabaitype cardiac glycosides such as deslanoside and digoxin even if such cardiac glycosides have identical genin structures.

Example 9: Quantitative Determination of Cardiac Glycoside Contained in Pharmaceutical Preparations and Pharmaceutical Ingredients by the Immunocapturing Method (ELISA Method) of the Present Invention The amounts of cardiac glycoside contained in the following pharmaceutical preparations and pharmaceutical ingredients were determined in the same manner as Example 8.

Pharmaceutical Preparation: Kyushin (Kyushin Pharmaceutical Code No. BA6653, Lot No. L20)

Pharmaceutical Ingredient: Senso (Tochigi Tenkaido, Lot No. 30607-Z)

In addition, bufaline (Sigma Chemical Co., Code No. B-0261) was used for the standard substance. The Kyushin sample solution and Senso sample solution used in testing were obtained in the manner described below.

Kyushin Sample Solution

Kyushin was ground in a mortar after wrapping in pharmaceutical wrapping paper and crushing. 175.6 mg of the ground powder was then weighed out. After adding 10 ml of boiling n-propanol and stirring vigorously, the solution was allowed to cool while stirring frequently. This solution was filtered using absorbent cotton soaked in n-propanol. The filtrate was transferred to a separatory funnel followed by extraction after adding 20 ml of water and 25 ml of chloroform. Extraction was repeated with a mixture of 25 ml of chloroform and 5 ml of n-propanol. The extract was washed each time with 5 ml of water. The extract was then filtered using absorbent cotton soaked in chloroform. The filtrate was evaporated with a rotary evaporator to obtain the sample solution by dissolving the residue in 1 ml of ethanol.

Senso Sample Solution

After shaving Senso into smaller fragments and grounding with a mortar, 1.0 g of the powder was weighed out. After adding 10 ml of boiling n-propanol and stirring vigorously, the solution was allowed to cool while stirring frequently. The solution was then filtered using absorbent cotton soaked in n-propanol. The filtrate was transferred to a separatory funnel followed by extraction after adding 20 ml of water and chloroform. Extraction was repeated with a mixture of 25 ml of chloroform and 5 ml of n-propanol. The extract was washed with 5 ml of water each time. The extract was filtered using absorbent cotton soaked in chloroform and the filtrate was evaporated with a rotary evaporator. The residue was dissolved in 1 ml of ethanol to obtain the sample solution.

Figure 13:
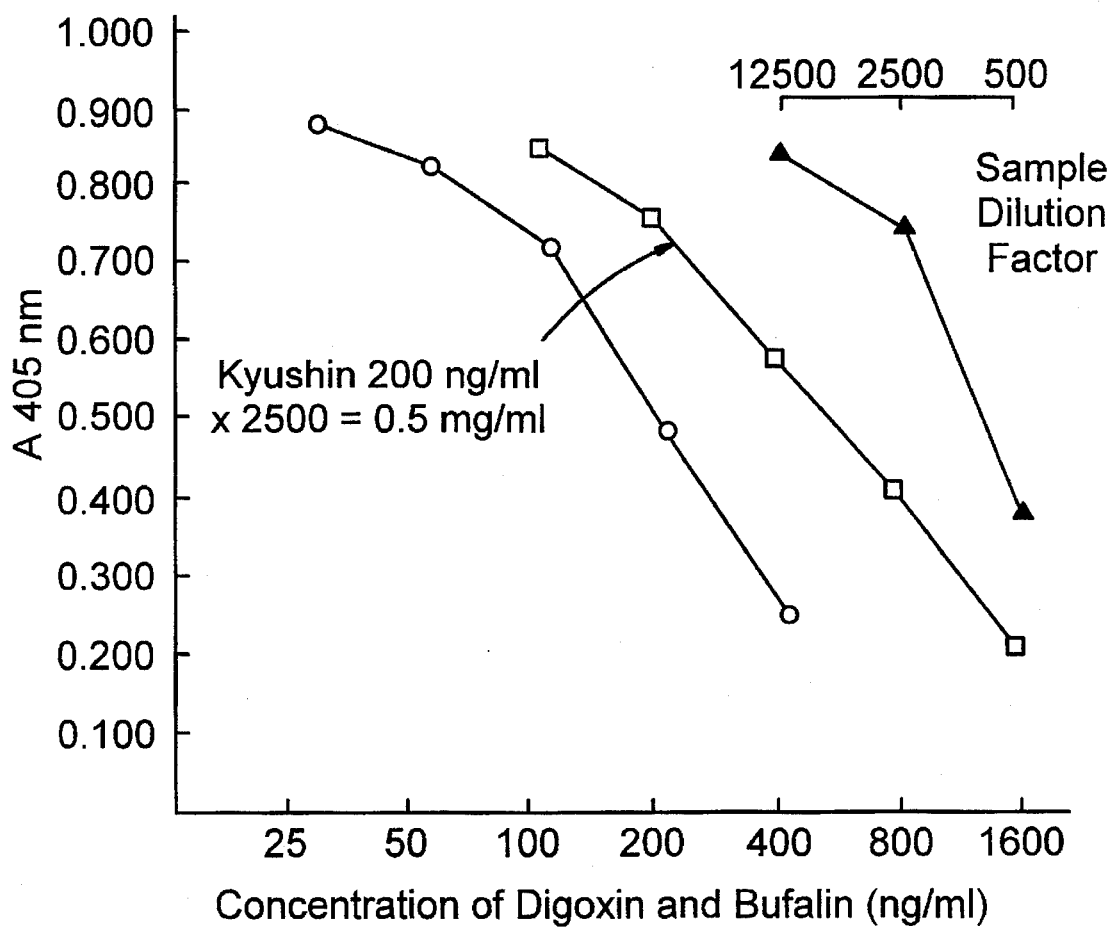
FIG. 13 is a graph using quantitative determination of a cardiac substance such as bufalin, which is contained in cardiac tablets, by EUSA.
Figure 14:
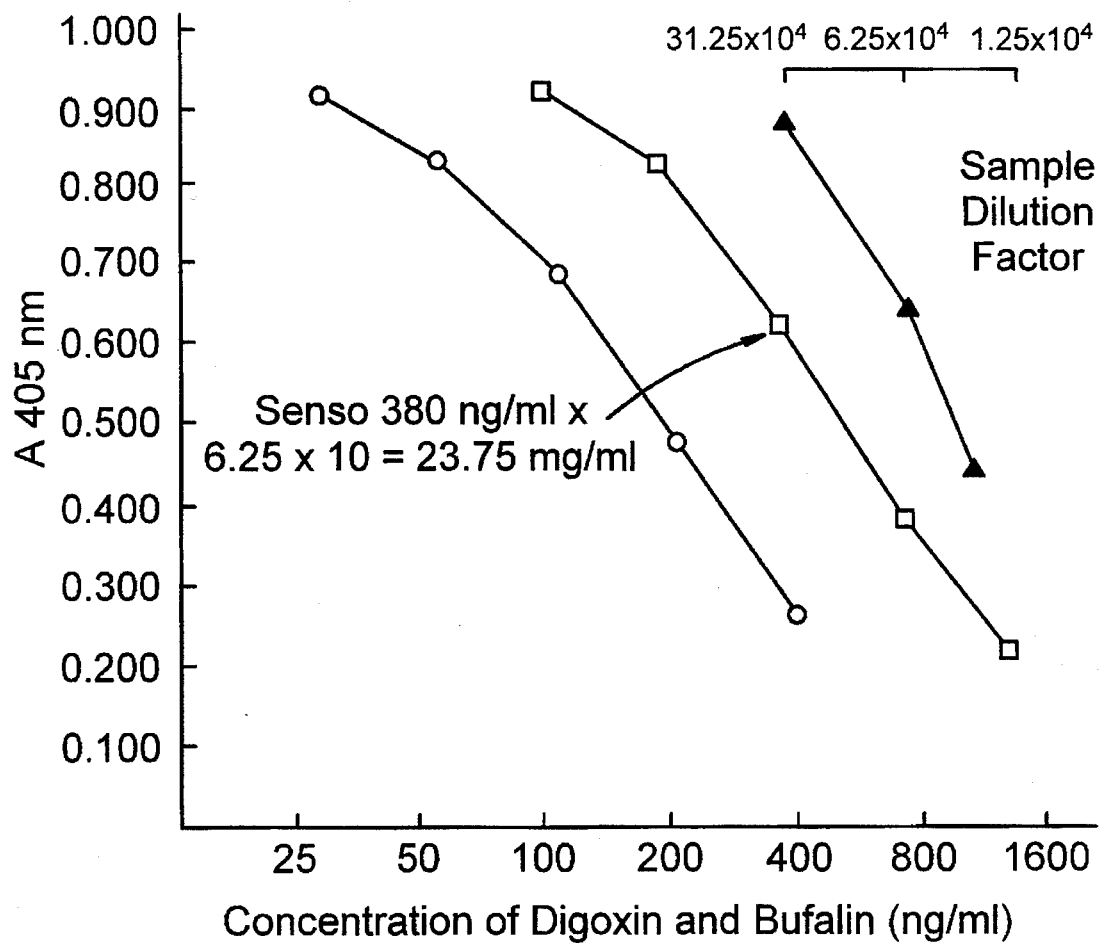
FIG. 14 is a graph used in quantitative determination of a cardiac substance such as bufalin, which is contained in Senso (raw drug ingredient), by EUSA.

The results of quantitative determination are indicated in FIG. 13, FIG. 14 and Table 8. As can be understood from these results, cardiac substances in pharmaceutical preparations or pharmaceutical ingredients, such as Kyushin and Senso, can be quantitatively determined by ELISA using the monoclonal antibody of the present invention. The cardiac steroid components contained in Kyushin and Senso consist of bufaline, regibufogenin, cinobufagin, bufotalin, cinobufotaline, gamabufotalin, telocinobufagin and hellebrigenin, etc. (Karigome, T. et al. (1976), Japanese Pharmacopoeia Guidebook, 9th Edition, Japan Official Documentation Association, Hirokawa Shoten, Tokyo D-512–D-515), and these substances are considered to be measured. Although the method employed for extracting cardiac substance from pharmaceutical preparations and pharmaceutical ingredients is simple in this case, in order to precisely measure the content of cardiac substances, the extraction method should be modified such as by extracting by heating and refluxing.

TABLE 8

Concentrations of Cardiac Substances Contained in Kyushin and Senso

| Sample | Concentration of Extracted Cardiac Substance | Concentration of Cardiac Substance in Pharmaceutical Preparations and their Ingredients |
| --- | --- | --- |
| Kyushin | 500 µg bufaline/ml | 43.0 µg bufaline/tablet |
| Senso | 23.8 mg bufaline/ml | 23.8 mg bufaline/g Senso |

Figure 15:
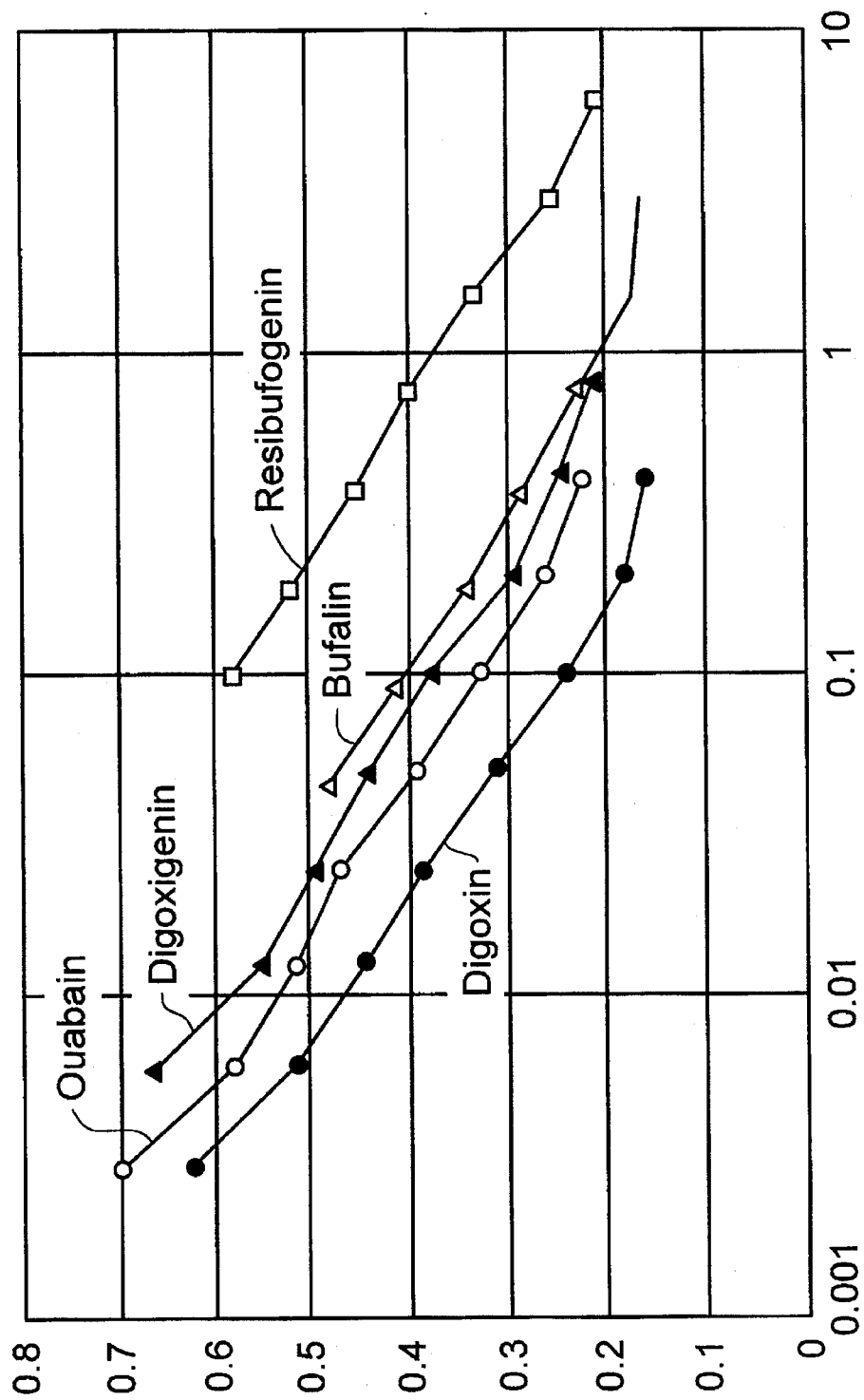
FIG. 15 is a graph indicating the relationship between absorbance and cardiac glycoside concentration as measured by ELISA using a monoclonal antibody of the present invention.

Example 10: Affinity of Various Cardiac Glycosides and the Antibody of the Present Invention According to the Immunocapturinq Method (ELISA) of the Present Invention The affinity between the antibody of the present invention and digoxin, ouabain, digoxigenin, bufaline and regibufogenin was evaluated in the same manner as Example 8. The results obtained are described in FIG. 15.

Cardiac glycosides having partial structures of a cis-bonded D-ring within the steroid structure as well as an accompanying methyl group bonded in the β-configuration at the C13 position, a hydroxyl group bonded in the β-configuration at the C14 position, and an α, β-unsaturated lactone group bonded in the β-configuration at the C17 position demonstrated strong affinity with the antibody (40 ng/ml to 400 ng/ml). In addition, it was also verified that when the oxygen atom of β-OH of the C14 position was substituted with an ether-bonded group in the β-configuration between the C14 and C15 positions, affinity decreased remarkably (100 ng/ml to 4 µg/ml).

Industrial Applicability

The monoclonal antibody of the present invention recognizes a specific structure of the steroid structural portion of cardiac glycoside, and is useful for measurement, recovery, purification, assay, selection and so forth of cardiac glycosides.

Reference to Deposited Microorganisms under Rule 13-2 and

Depository Authority: Fermentation Research Institute, Agency of Industrial Science and Technology 1-1-3 Higashi, Tsukuba, Ibaraki Mouse hybridoma cell line SBM319
FERM BP-3197 Deposited on Dec. 12, 1990
Mouse hybridoma cell line SBM320
FERM BP-3198 Deposited on Dec. 12, 1990

We claim:

1. A method for the detection of a physiologically active substance having potassium ion concentration antagonist type $Na^+$, $K^+$,-ATPase activity inhibitory action comprising the steps of:

(i) reacting a test sample with a monoclonal antibody produced using an ouabain-protein complex as the immunogen which specifically binds to the steroid structures of all of the following compounds (a), (b), (c) and (d):

(a) a cardiac glycoside represented the formula (I-a):

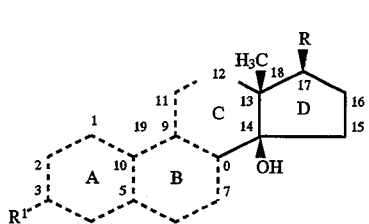

wherein, R represents the following cardenolide form:

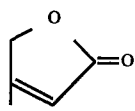

$R^1$ represent a sugar group represented by the formula:

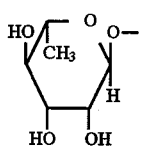

and wherein the D-ring is bonded to the C-ring in the cis-conformation, and the B-ring is bonded to the A-ring in the cis or trans-configuration;

(b) a cardiac glycoside represented by the formula (I-b):

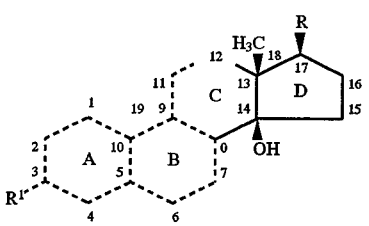

wherein, R represents the following bufagenolide form:

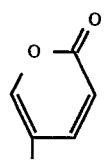

$R^1$ represent a sugar group represented by the formula:

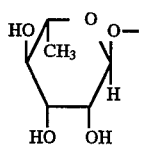

and wherein the D-ring is bonded to the C-ring in the cis-conformation, and the B-ring is bonded to the A-ring in the cis or trans-configuration;

(c) an aglycone of a cardiac glycoside represented by the formula (I-c):

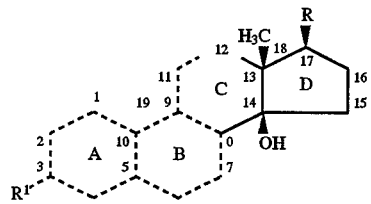

wherein, R represents the following cardenolide form:

$R^1$ represent a hydroxyl group, and wherein the D-ring is bonded to the C-ring in the cis-conformation, and the B-ring is bonded to the A-ring in the cis or transconfiguration;

(d) an aglycone of a cardiac glycoside represented by the formula (I-d):

wherein, R represents the following bufagenolide form:

$R^1$ represents a hydroxyl group, and wherein the D-ring is bonded to the C-ring in the cis-conformation, and the B-ring is bonded to the A-ring in the cis-or trans-configuration;

wherein the compounds (a) to (d) have an inhibitory action to $Na^+$, $K^+$-ATPase activity as a potassium ion concentration antagonist;

(ii) detecting a complex of the monoclonal antibody and the physiologically active substance; and (iii) correlating the detected complex with the presence of the physiologically active substance in the test sample;

wherein one monoclonal antibody can detect any of the physiologically active substance represented by said formula (a), (b), (c) or (d).

2. A method for separation or purification of a physiologically active substance having potassium ion concentration antagonist $Na^+$, $K^+$-ATPase activity inhibitory action, comprising the steps of contacting said substance with a monoclonal antibody so as to bind the substance to the monoclonal antibody under conditions which result in a complex, separating the resultant complex, dissociating the complex, and recovering the substance from the monoclonal antibody;

wherein said monoclonal antibody produced using an ouabain-protein complex as the immunogen specifically binds to the steroid structures of all of the following compounds (a), (b), (c) and (d):

(a) a cardiac glycoside represented by the formula (I-a):

(I-a)

wherein, R represents the following cardenolide form:

$R^1$ represent a sugar group represented by the formula:

and wherein the D-ring is bonded to the C-ring in the cis-conformation, and the B-ring is bonded to the A-ring in the cis or trans-configuration;

(b) a cardiac glycoside represented by the formula (I-b):

(I-b)

wherein, R represents the following bufagenolide form:

$R^1$ represent a sugar group represented by the formula:

and wherein the D-ring is bonded to the C-ring in the cis-conformation, and the B-ring is bonded to the A-ring in the cis or trans-configuration.

(c) an aglycone of a cardiac glycoside represented by the formula (I-c):

(I-c)

wherein, R represents the following cardenolide form:

$R^1$ represents a hydroxyl group, and wherein the D-ring is bonded to the C-ring in the cis-conformation, and the B-ring is bonded to the A-ring in the cis or transconfiguration;

(d) an aglycone of a cardiac glycoside represented by the formula (I-d):

(I-d)

wherein, R represents the following bufagenolide form:

$R^1$ represents a hydroxyl group, and wherein the D-ring is bonded to the C-ring in the cis-conformation, and the B-ring is bonded to the A-ring in the cis or trans-configuration;

wherein the compounds (a) to (d) have an inhibitory action to $Na^+$, $K^+$-ATPase activity as a potassium ion concentration antagonist;

wherein one monoclonal antibody can separate or purify any of the physiologically active substance represented by said formula (a), (b), (c) or (d).

3. The method of claim 2, wherein the monoclonal antibody is produced by hybridoma 249F8 (FERM BP-3197) or hybridoma 278A9 (FERM BP-3198) or a cell line derived from either of said hybridomas.

* * * * *